US011666324B2

(12) United States Patent
Bagaoisan et al.

(10) Patent No.: US 11,666,324 B2
(45) Date of Patent: Jun. 6, 2023

(54) APPARATUS AND METHODS FOR TISSUE CLOSURE

(71) Applicant: TELEFLEX MEDICAL INCORPORATED, Morrisville, NC (US)

(72) Inventors: Celso Bagaoisan, Union City, CA (US); Suresh Pai, Mountain View, CA (US); James Dreher, Santa Monica, CA (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 448 days.

(21) Appl. No.: 16/695,061

(22) Filed: Nov. 25, 2019

(65) Prior Publication Data

US 2020/0163667 A1 May 28, 2020

Related U.S. Application Data

(63) Continuation of application No. 15/583,879, filed on May 1, 2017, now Pat. No. 10,485,533, which is a
(Continued)

(51) Int. Cl.
*A61B 17/04* (2006.01)
*A61B 17/00* (2006.01)
(Continued)

(52) U.S. Cl.
CPC ...... *A61B 17/0482* (2013.01); *A61B 17/0057* (2013.01); *A61B 17/0469* (2013.01);
(Continued)

(58) Field of Classification Search
CPC ............ A61B 17/0482; A61B 17/0469; A61B 17/0493; A61B 2017/00858;
(Continued)

(56) References Cited

U.S. PATENT DOCUMENTS 2,646,045 A 7/1953 Priestley
3,361,382 A 1/1968 Converse
(Continued)

FOREIGN PATENT DOCUMENTS

EP 1 254 635 A1 11/2002
EP 2012675 A2 1/2009
(Continued)

OTHER PUBLICATIONS

International Search Report and Written Opinion dated Sep. 9, 2013, issued in corresponding International Application No. PCT/US2013/020094.

*Primary Examiner* — Julian W Woo
(74) *Attorney, Agent, or Firm* — BakerHostetler

(57) ABSTRACT

Apparatus and methods are provided for treating a tissue opening, for example a trocar opening used in a minimally invasive surgical procedure. In a tissue closure device, a finger guard or shield can be used, handle or holding area or areas can be used, and positioning indicators can be used. A resiliently flexible target material can also be used for reliably holding a suture during the procedure. Introducers can be used having a suture holder, an alignment indicator and insertion limits.

14 Claims, 11 Drawing Sheets

Related U.S. Application Data continuation of application No. 14/589,647, filed on Jan. 5, 2015, now Pat. No. 9,636,105, which is a continuation of application No. 13/144,291, filed as application No. PCT/US2010/020652 on Jan. 11, 2010, now Pat. No. 8,926,639.

(60) Provisional application No. 61/144,151, filed on Jan. 12, 2009.

(51) Int. Cl.
    *A61B 17/06*          (2006.01)
    *A61B 17/29*          (2006.01)

(52) U.S. Cl.
    CPC ............ *A61B 17/0493* (2013.01); *A61B 2017/00637* (2013.01); *A61B 2017/00663* (2013.01); *A61B 2017/00672* (2013.01); *A61B 2017/00858* (2013.01); *A61B 2017/0472* (2013.01); *A61B 2017/06042* (2013.01); *A61B 2017/2911* (2013.01); *A61B 2017/2946* (2013.01)

(58) Field of Classification Search
    CPC .... A61B 2017/0472; A61B 2017/2911; A61B 2017/00663; A61B 2017/06042; A61B 17/0057; A61B 2017/00637; A61B 2017/2946

See application file for complete search history.

(56) References Cited

U.S. PATENT DOCUMENTS

| | | | |
|---|---|---|---|
| 3,399,668 A | 9/1968 | Lundgren | |
| 3,577,991 A | 5/1971 | Wilkinson | |
| 3,877,434 A | 4/1975 | Ferguson et al. | |
| 4,345,602 A | 8/1982 | Yoshimura et al. | |
| 4,493,323 A | 1/1985 | Albright et al. | |
| 4,526,173 A | 7/1985 | Sheehan | |
| 4,553,543 A | 11/1985 | Amarasinghe | |
| 4,621,640 A | 11/1986 | Mulhollan et al. | |
| 4,674,501 A | 6/1987 | Greenberg | |
| 4,744,353 A | 5/1988 | McFarland | |
| 4,744,364 A | 5/1988 | Kensey | |
| 4,899,743 A | 2/1990 | Nicholson et al. | |
| 4,938,214 A | 7/1990 | Specht et al. | |
| 4,950,273 A | 8/1990 | Briggs | |
| 4,955,384 A | 9/1990 | Taylor et al. | |
| 4,995,865 A | 2/1991 | Gahara et al. | |
| 5,009,663 A | 4/1991 | Broome | |
| 5,015,250 A | 5/1991 | Foster | |
| 5,037,433 A | 8/1991 | Wilk et al. | |
| 5,041,129 A | 8/1991 | Hayhurst et al. | |
| 5,053,043 A | 10/1991 | Gottesman et al. | |
| 5,078,721 A | 1/1992 | McKeating | |
| 5,100,417 A | 3/1992 | Cerier et al. | |
| 5,127,785 A | 3/1992 | Faucher | |
| 5,147,373 A | 9/1992 | Ferzli | |
| 5,171,256 A | 12/1992 | Smith et al. | |
| 5,171,257 A | 12/1992 | Ferzli | |
| 5,176,691 A | 1/1993 | Pierce | |
| 5,181,919 A | 1/1993 | Bergman et al. | |
| 5,192,298 A | 3/1993 | Smith et al. | |
| 5,196,023 A | 3/1993 | Martin | |
| 5,201,743 A | 4/1993 | Haber et al. | |
| 5,201,744 A | 4/1993 | Jones | |
| 5,201,752 A | 4/1993 | Brown et al. | |
| 5,201,759 A | 4/1993 | Ferzli | |
| 5,211,655 A | 5/1993 | Hasson | |
| 5,220,926 A | 6/1993 | Jones | |
| 5,222,508 A | 6/1993 | Contarini | |
| 5,222,977 A | 6/1993 | Esser | |
| 5,226,899 A | 7/1993 | Lee et al. | |
| 5,234,444 A | 8/1993 | Christoudias | |
| 5,269,772 A | 12/1993 | Wilk | |
| 5,281,237 A | 1/1994 | Gimpelson | |
| 5,304,184 A | 4/1994 | Hathaway et al. | |
| 5,306,278 A | 4/1994 | Dahl et al. | |
| 5,308,358 A | 5/1994 | Bond et al. | |
| 5,320,632 A | 6/1994 | Heidmueller | |
| 5,334,200 A | 8/1994 | Johnson | |
| 5,342,391 A | 8/1994 | Foshee et al. | |
| 5,364,408 A | 11/1994 | Gordon | |
| 5,374,275 A | 12/1994 | Bradley et al. | |
| 5,387,221 A | 2/1995 | Bisgaard | |
| 5,391,182 A | 2/1995 | Chin | |
| 5,417,699 A | 5/1995 | Klein et al. | |
| 5,458,609 A | 10/1995 | Gordon et al. | |
| 5,476,469 A | 12/1995 | Hathaway et al. | |
| 5,480,409 A | 1/1996 | Riza | |
| 5,496,335 A | 3/1996 | Thomason et al. | |
| 5,501,692 A | 3/1996 | Riza | |
| 5,507,755 A | 4/1996 | Gresl et al. | |
| 5,507,758 A | 4/1996 | Thomason et al. | |
| 5,522,839 A | 6/1996 | Pilling | |
| 5,527,321 A | 6/1996 | Hinchliffe | |
| 5,527,322 A | 6/1996 | Klein et al. | |
| 5,562,686 A | 10/1996 | Sauer et al. | |
| 5,562,688 A | 10/1996 | Riza | |
| 5,571,117 A | 11/1996 | Ahn | |
| 5,573,495 A | 11/1996 | Adler | |
| 5,601,576 A | 2/1997 | Garrison | |
| 5,613,974 A | 3/1997 | Andreas et al. | |
| 5,618,290 A | 4/1997 | Toy et al. | |
| 5,700,273 A | 12/1997 | Buelna et al. | |
| 5,716,369 A | 2/1998 | Riza | |
| 5,746,755 A | 5/1998 | Wood et al. | |
| 5,772,678 A | 6/1998 | Thomason et al. | |
| 5,782,749 A | 7/1998 | Riza | |
| 5,792,152 A | 8/1998 | Klein et al. | |
| 5,810,850 A | 9/1998 | Hathaway et al. | |
| 5,817,111 A | 10/1998 | Riza | |
| 5,827,299 A | 10/1998 | Thomason et al. | |
| 5,827,300 A | 10/1998 | Fleega | |
| 5,843,122 A | 12/1998 | Riza | |
| 5,860,990 A | 1/1999 | Nobles et al. | |
| 5,868,784 A | 2/1999 | Riza | |
| 5,899,911 A | 5/1999 | Carter | |
| 5,921,918 A | 7/1999 | Riza | |
| 5,928,256 A | 7/1999 | Riza | |
| 5,935,126 A | 8/1999 | Riza | |
| 5,954,732 A | 9/1999 | Hart et al. | |
| 5,954,734 A | 9/1999 | Thomason et al. | |
| 5,964,773 A | 10/1999 | Greenstein | |
| 5,993,471 A | 11/1999 | Riza et al. | |
| 6,015,428 A | 1/2000 | Pagedas | |
| 6,059,800 A | 5/2000 | Hart et al. | |
| 6,117,144 A | 9/2000 | Nobles et al. | |
| 6,136,010 A | 10/2000 | Modesitt et al. | |
| 6,183,485 B1 | 2/2001 | Thomason et al. | |
| 6,245,079 B1 | 6/2001 | Nobles et al. | |
| 6,273,871 B1 * | 8/2001 | Davis ............... | A61M 25/0637 |
| | | | 604/164.05 |
| 6,383,199 B2 | 5/2002 | Carter et al. | |
| 6,464,691 B1 | 10/2002 | Castaneda et al. | |
| 6,517,553 B2 | 2/2003 | Klein et al. | |
| 6,551,331 B2 | 4/2003 | Nobles et al. | |
| 6,562,052 B2 | 5/2003 | Nobles et al. | |
| 6,911,034 B2 | 6/2005 | Nobles et al. | |
| 6,939,356 B2 | 9/2005 | Debbas | |
| 7,911,905 B2 | 3/2011 | Park | |
| 8,066,718 B2 | 11/2011 | Weisel et al. | |
| 8,491,609 B2 | 7/2013 | Stone | |
| 8,876,840 B2 * | 11/2014 | Harada ............. | A61B 17/0469 |
| | | | 606/144 |
| 9,636,105 B2 | 5/2017 | Bagaoisan et al. | |
| 9,820,771 B2 * | 11/2017 | Norton ............... | A61B 17/3423 |
| 10,485,533 B2 * | 11/2019 | Bagaoisan .......... | A61B 17/0493 |
| 2001/0031973 A1 | 10/2001 | Nobles et al. | |
| 2002/0045908 A1 | 4/2002 | Nobles et al. | |
| 2004/0068273 A1 | 4/2004 | Fariss et al. | |
| 2004/0220592 A1 | 11/2004 | Mueller et al. | |
| 2004/0236353 A1 | 11/2004 | Bain et al. | |
| 2004/0249393 A1 | 12/2004 | Weisel et al. | |

(56) References Cited

U.S. PATENT DOCUMENTS

| | | |
|---|---|---|
| 2006/0030868 A1 | 2/2006 | Bennett et al. |
| 2007/0203507 A1 | 8/2007 | McLaughlin et al. |
| 2007/0213757 A1 | 9/2007 | Boraiah |
| 2008/0033459 A1 | 2/2008 | Shafi et al. |
| 2008/0045979 A1 | 2/2008 | Ma |
| 2010/0016870 A1 | 1/2010 | Campbell |
| 2015/0018850 A1 | 1/2015 | Bagaoisan et al. |

FOREIGN PATENT DOCUMENTS

| | | |
|---|---|---|
| EP | 2 305 129 A2 | 4/2011 |
| EP | 2412317 A1 | 2/2012 |
| EP | 2900149 A2 | 8/2015 |
| JP | 1142233 | 1/1997 |
| JP | 2001-524864 A | 12/2001 |
| JP | 200625932 | 2/2006 |
| SU | 1093329 A1 | 5/1984 |
| WO | 99/45848 A1 | 9/1999 |
| WO | 2007/025302 A1 | 3/2007 |
| WO | 2007/125279 A2 | 11/2007 |
| WO | 2010/081096 A2 | 7/2010 |
| WO | 2013/103682 A2 | 7/2013 |
| WO | 2013/103862 A1 | 7/2013 |
| WO | 2014/051930 A2 | 4/2014 |

\* cited by examiner

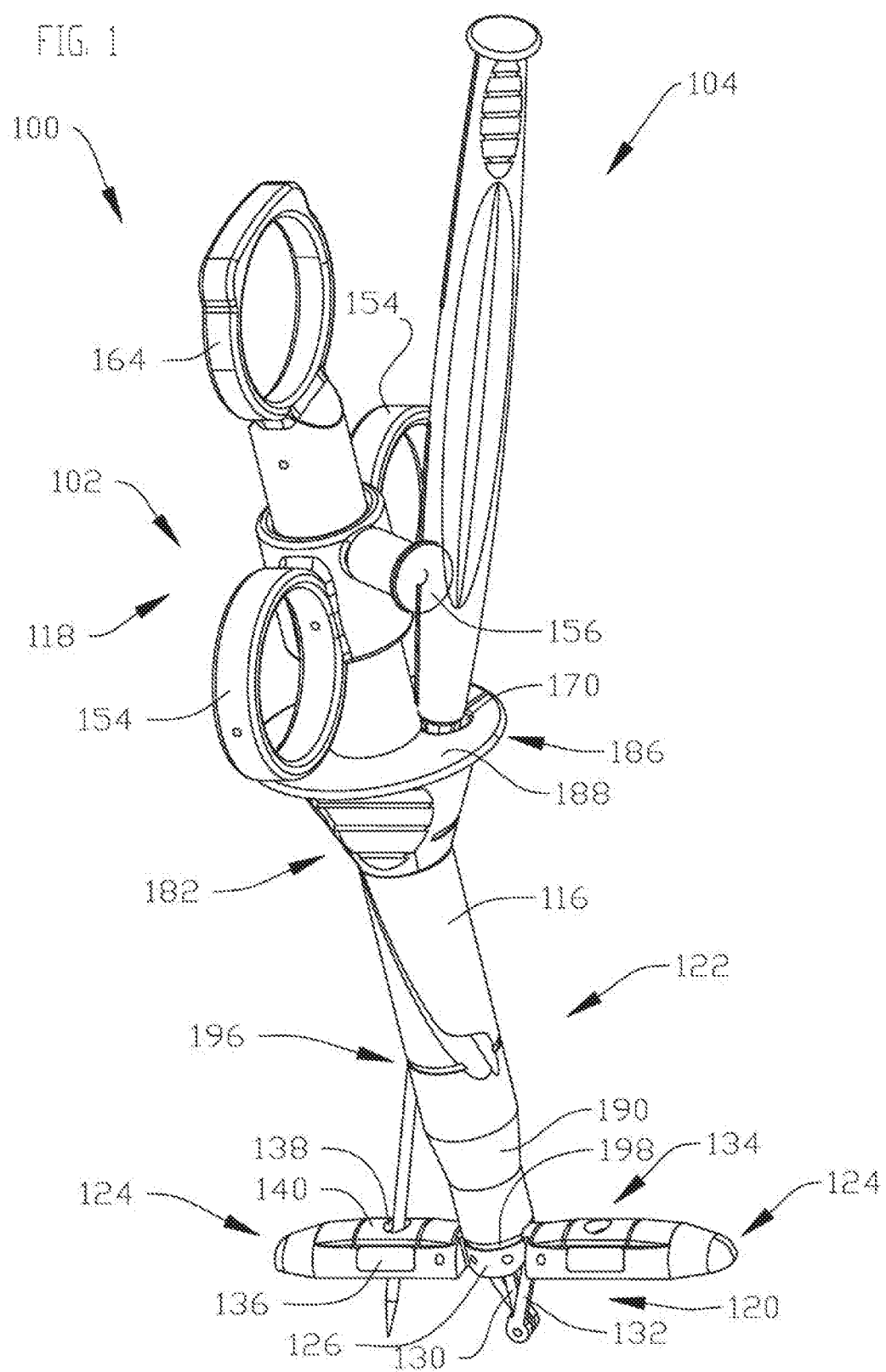

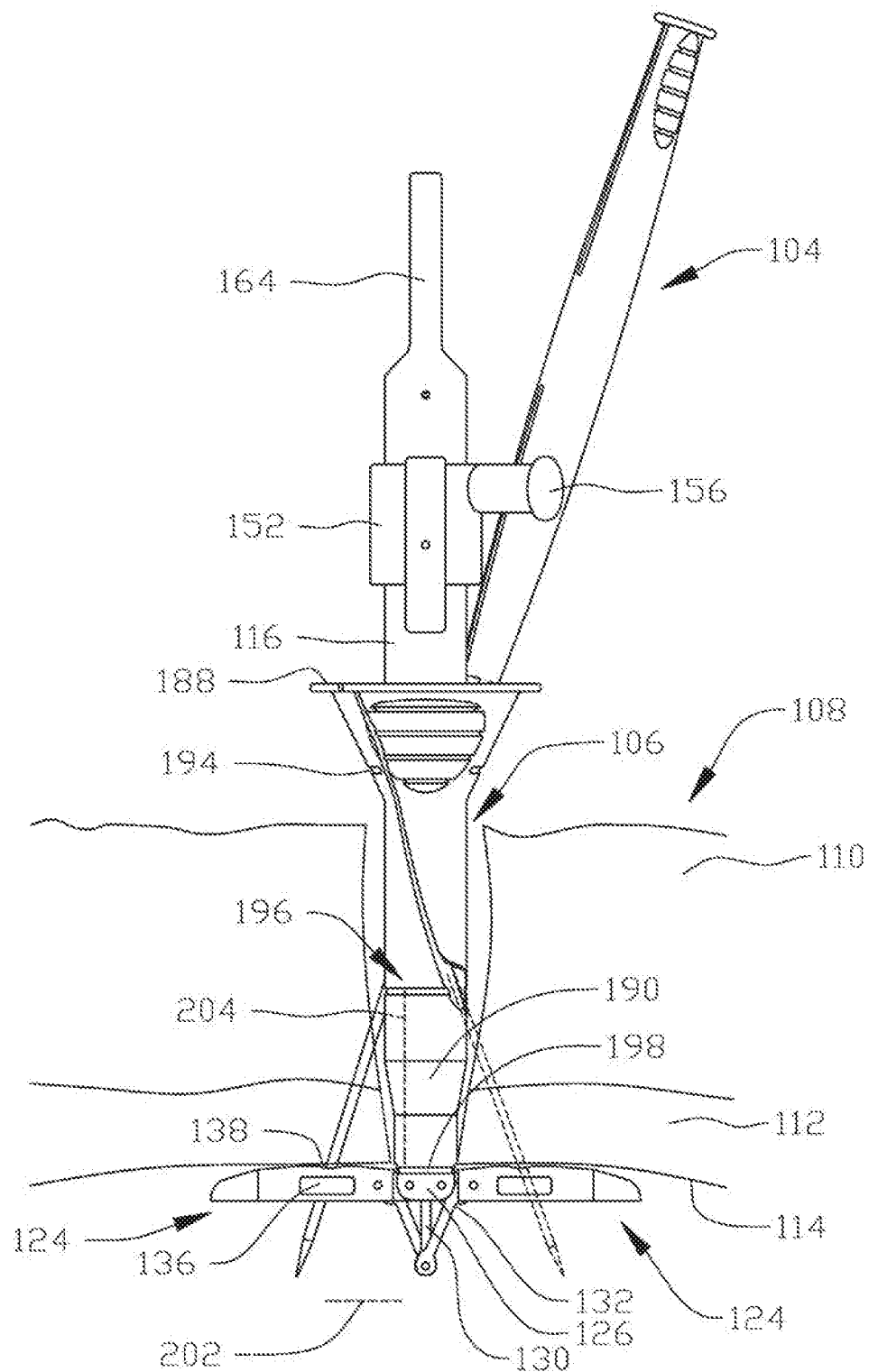

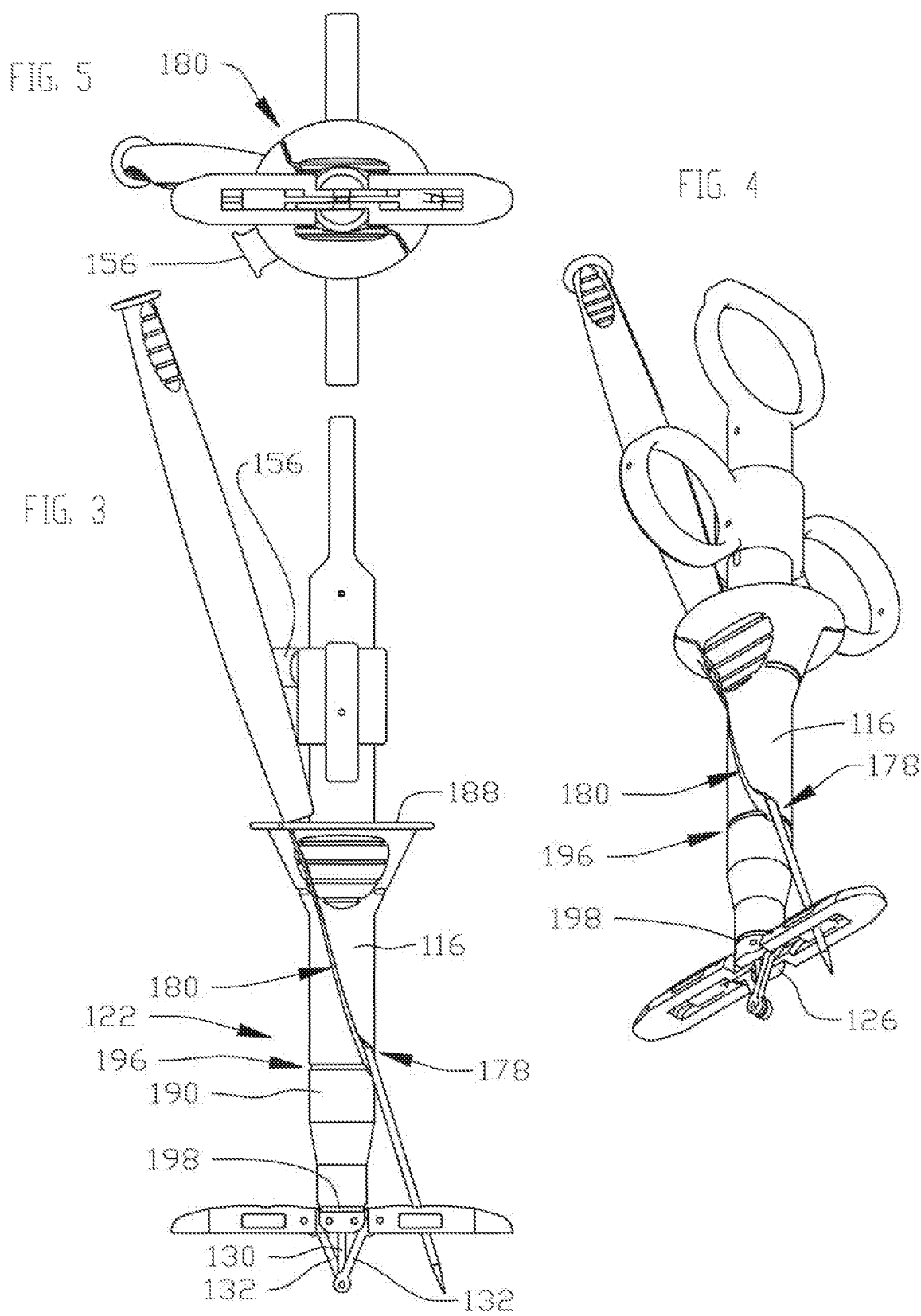

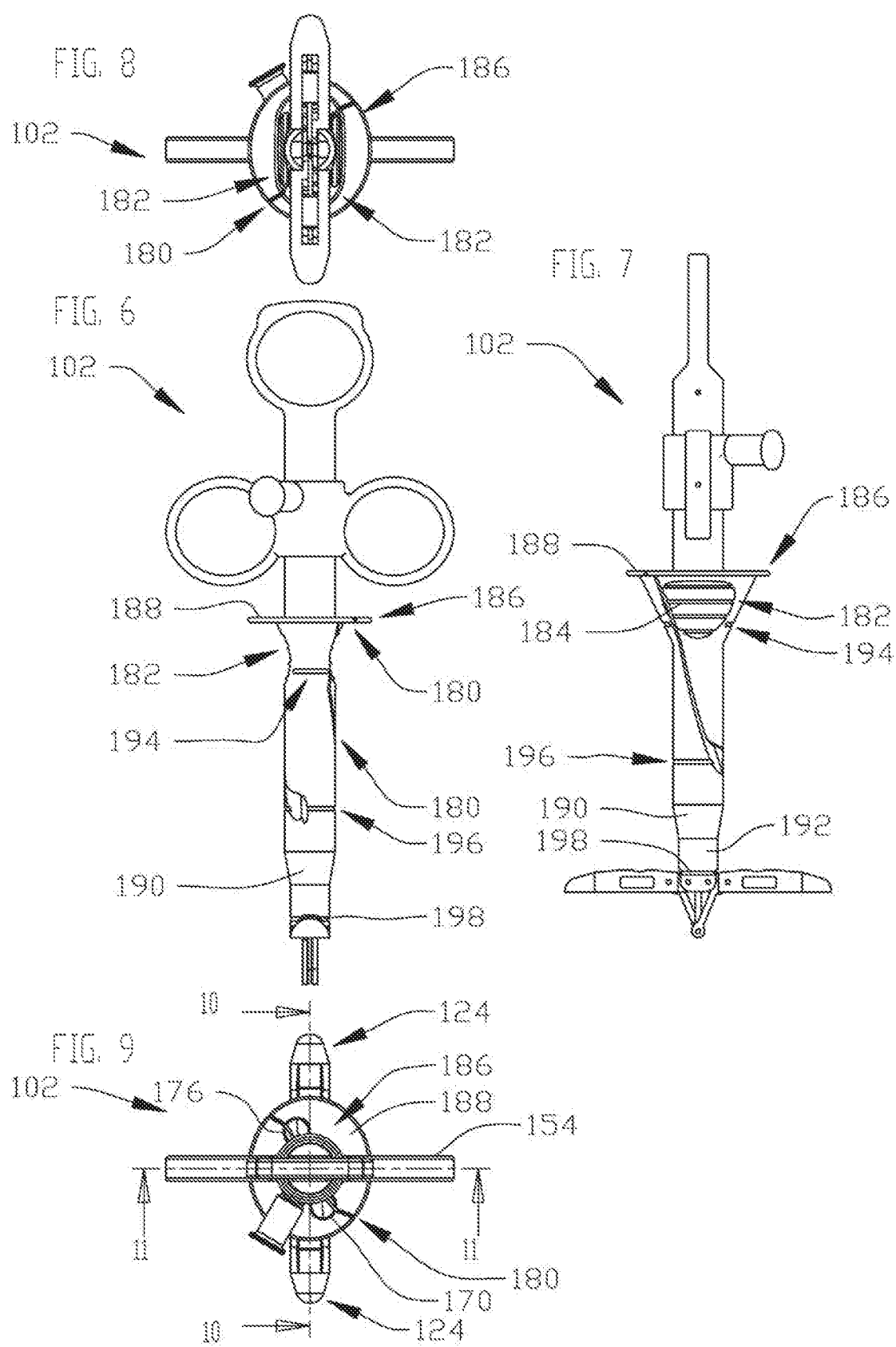

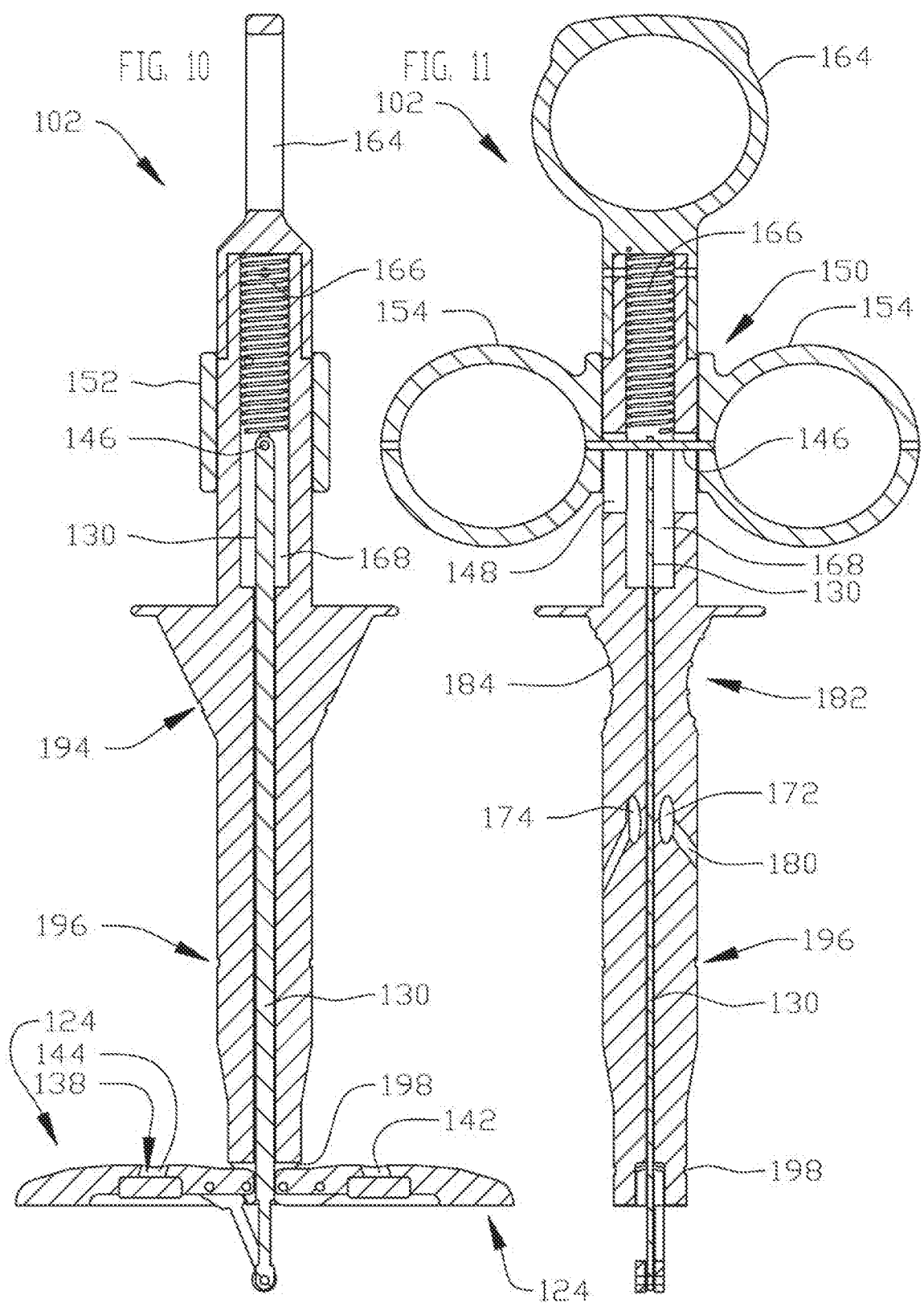

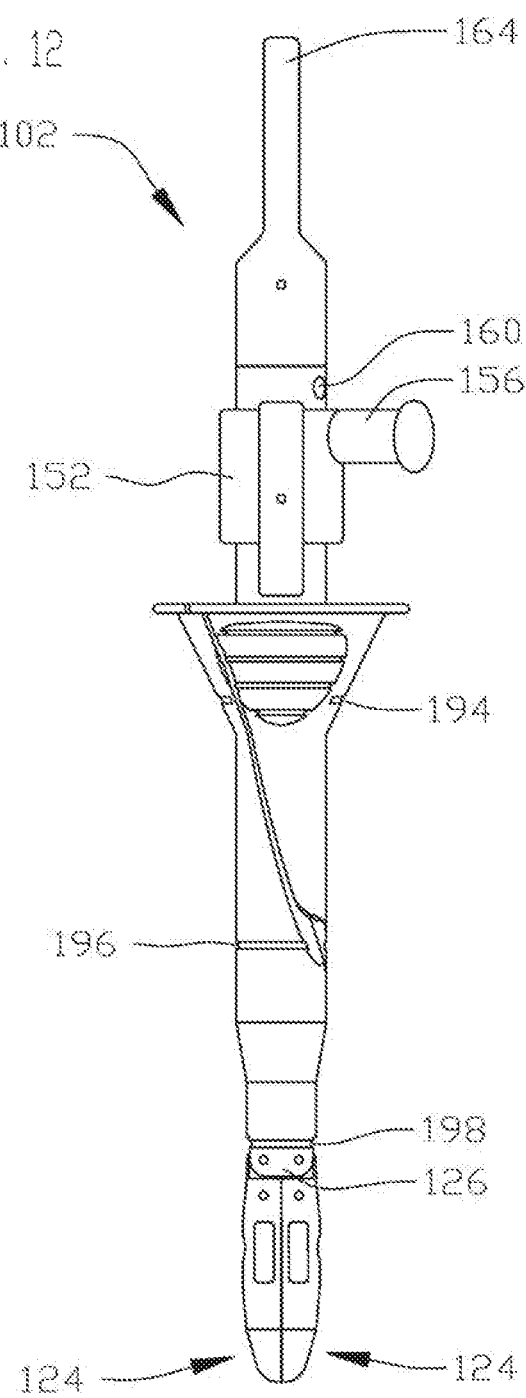

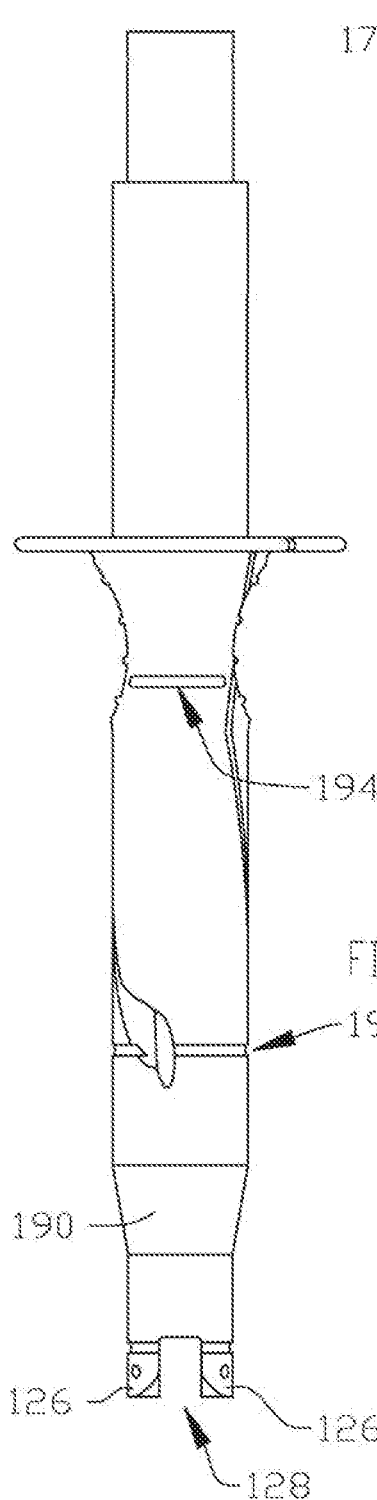
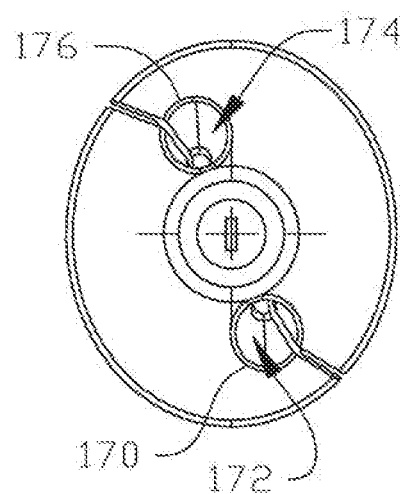
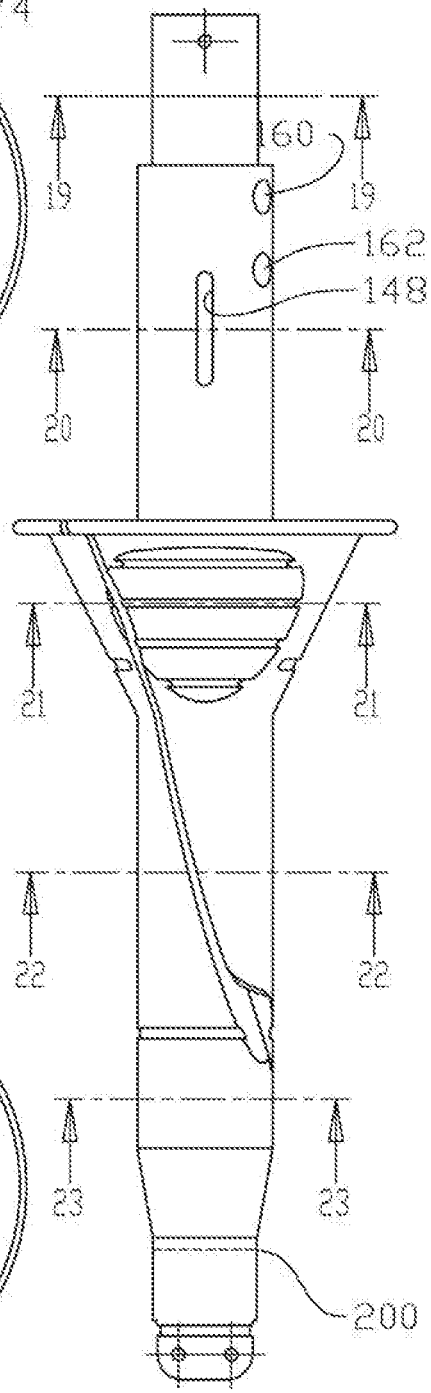
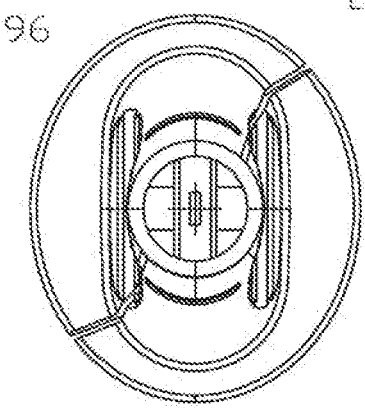

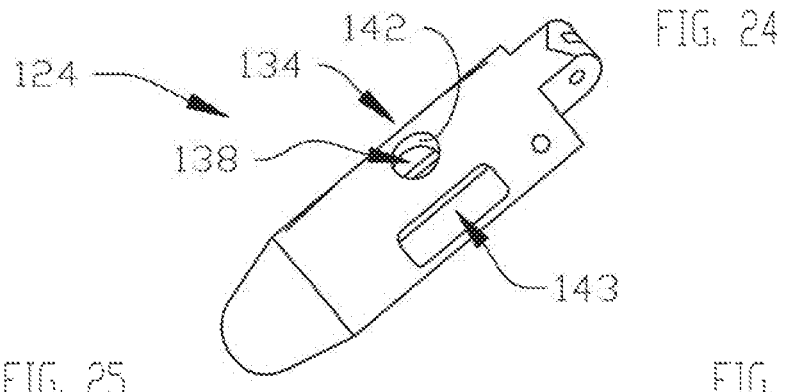
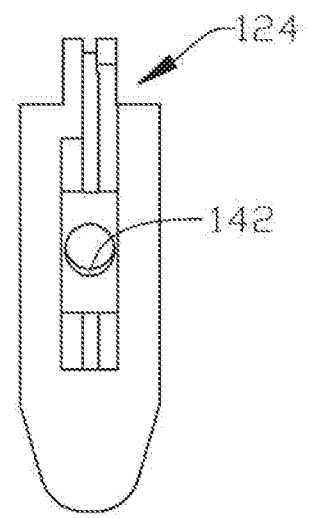
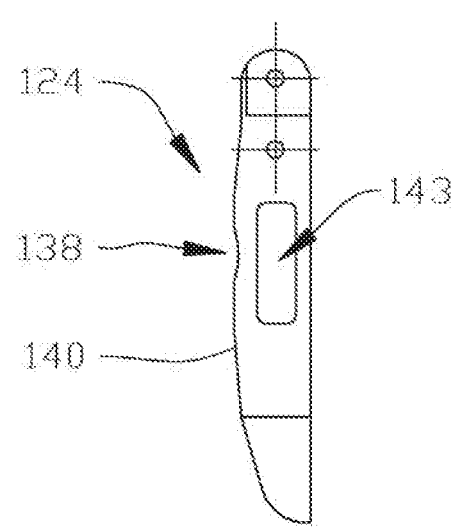
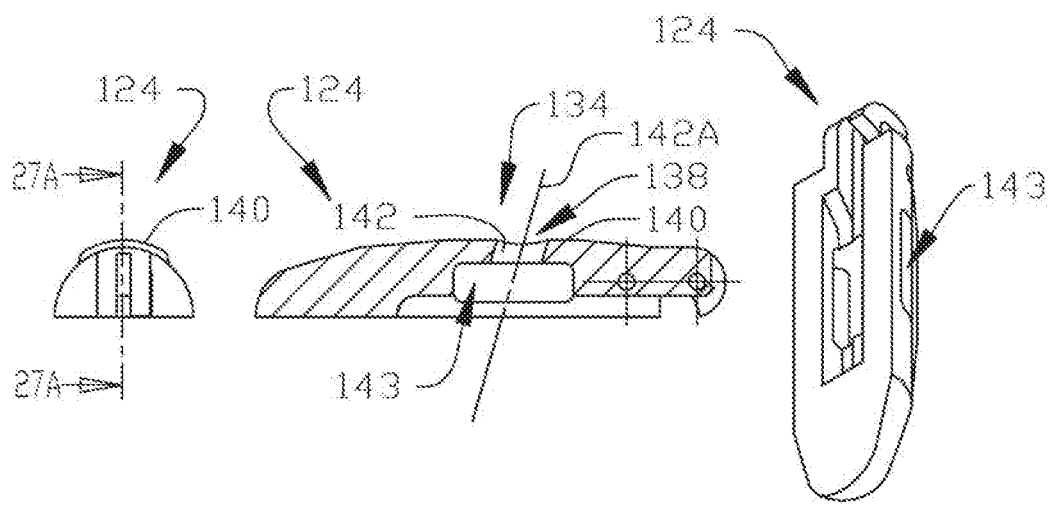

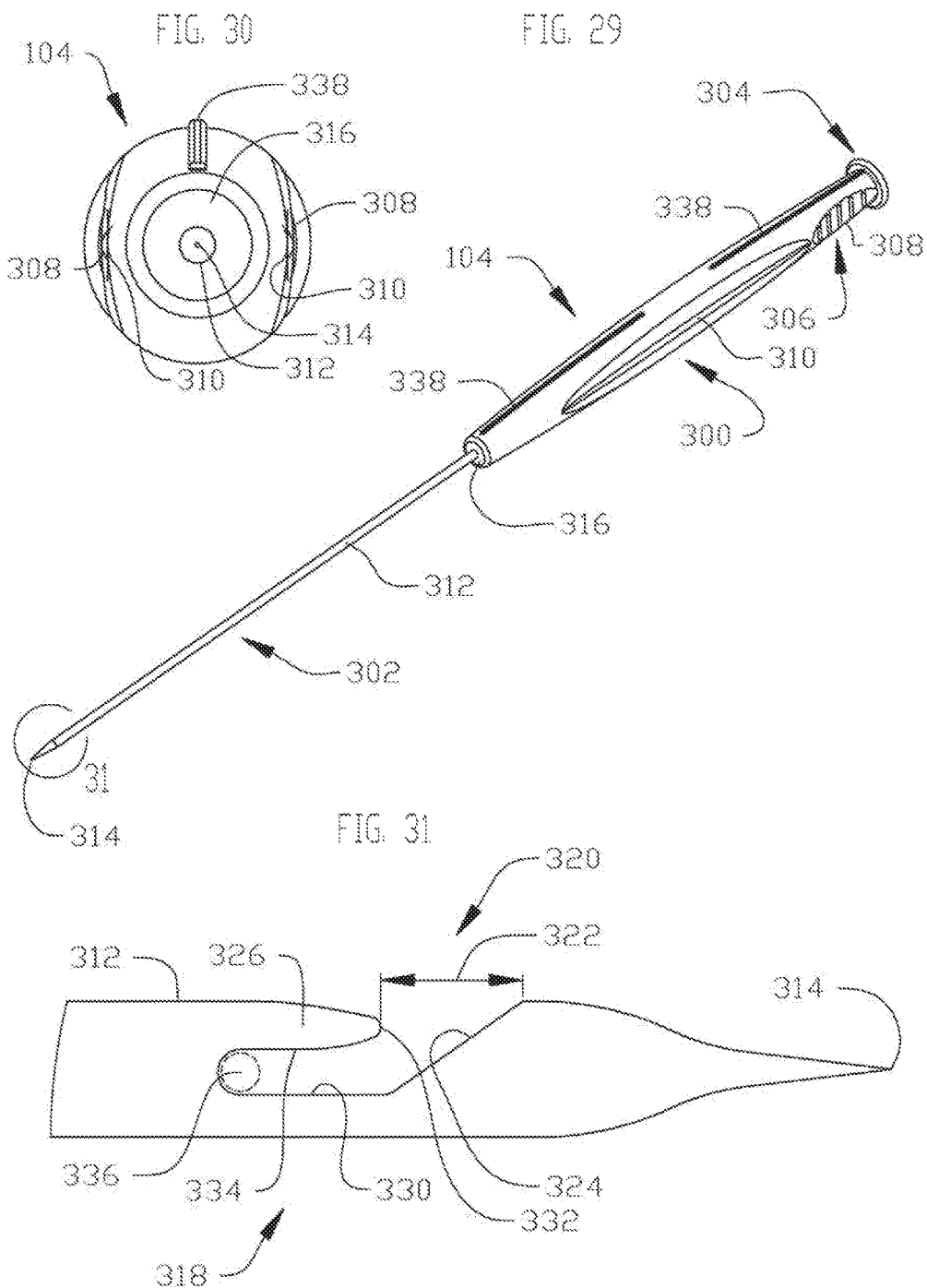

APPARATUS AND METHODS FOR TISSUE CLOSURE

CROSS-REFERENCE TO RELATED APPLICATION

This application is a continuation of U.S. patent application Ser. No. 15/583,879 (filed May 1, 2017, now U.S. Pat. No. 10,485,533), which is a continuation of U.S. patent application Ser. No. 14/589,647 (filed Jan. 5, 2015, now U.S. Pat. No. 9,636,105), which is a continuation of U.S. patent application Ser. No. 13/144,291 (filed Oct. 3, 2011, now U.S. Pat. No. 8,926,639), which is the national stage of International Application No. PCT/US2010/020652 (filed Jan. 11, 2010), which claims the benefit of U.S. Provisional Patent Application No. 61/144,151 (filed Jan. 12, 2009), the disclosures of which are hereby incorporated by reference as if set forth in their entireties herein.

BACKGROUND i. Field

This relates to tissue closure devices, including surgical suturing devices as well as such devices that can be used for intra-abdominal suturing and suturing of puncture wounds generated by surgical trocars and other puncturing devices.

ii. Related Art

Minimally invasive methods for conducting surgery on internal organs, tissues, ligaments and bones use extremely small instruments such as catheters, laparoscopes, and the like. The instruments are introduced using very small incisions, for example on the order of five to 18 mm in diameter, into which a trocar or other introducing device is placed. The trocars may have a diameter, for example, between 3 mm and 30 mm, with the smaller trocars leaving the opening substantially unchanged. The larger trocars may enlarge the opening. The trocars provide a reliable and fixed opening for introducing and removing various surgical instruments, viewing devices and other instruments used during the surgical procedure.

While the incisions and the trocar opening are quite small by traditional surgical standards, they still require closure after completing the surgical procedure. Surgical closure reduces the possibility of post-surgical infection, post-surgical herniation (for example in abdominal surgeries), subsequent bleeding or other effects. Closure can be accomplished either through manual suturing or suturing instruments used to complete the closure. In either case, suturing is made difficult by the small opening size, for example not only for manipulating the suture but also for visualizing the procedure. Closure is also made more difficult by the need to suture the subcutaneous tissue, for example fascial layers, separate from closure of the overlying skin, and doing so through a very small opening in the skin.

Conventional closure techniques such as those for closing openings in the abdominal wall pass sutures through the abdominal wall tissue a distance from the original trocar incision. One or more sutures are then tied off to close the subcutaneous layer followed by suitable closure of the skin layer. It has been noted that the distance of the suture location from the original incision opening is important in order to secure a suitable amount of abdominal wall tissue for forming a reliable closure. If the distance is too small, the closure may not be enough to reliably close the opening without later complications. See, for example, US Patent Publication 20060030868, incorporated herein by reference.

Tissue closure devices, for example laparoscopic port closure devices, may be introduced into the opening after removal of the trocar device to make easier the suturing of the trocar opening. Various methods and structures may help in closing the opening, but may require a significant number of steps for completing the closure, Some devices may require a significant amount of manual care in suturing the opening and tying off the suture, as well as close visualization for accomplishing the closure. Additionally, some devices have a significant number of components or special devices in order to accomplish the closure, or they may not provide consistent and reliable results even under normal operating circumstances.

SUMMARY

Apparatus and methods are provided that are easy to use for closing a tissue opening, for example a trocar opening used in a minimally invasive surgical procedure. One or more of the examples of the apparatus and methods described are easy to use and provide a reduced number of steps to produce a consistent and reliable closure. The apparatus and methods may be more simple than conventional techniques, and can be possibly done without scope visualization under appropriate circumstances. One or more of these features can be provided with the apparatus and methods described herein. In one example of apparatus and methods for closing a tissue opening, for example an abdominal trocar opening used in surgery, a closure device is used for closing the tissue opening. A passageway in the closure device, which in one example may be a trans-lateral passageway, is used to guide a needle or other suture carrier along the passageway and through a tissue layer to be closed. A surface or barrier formed on the closure device distal of an opening to the passageway helps to protect an operator's finger while a suture is being introduced to the passageway in the body. The surface or barrier may be a shield, disc, plate guard or other blocking element that can reduce the possibility of needle stick when an operator's finger or fingers are placed under the surface and the introducer is introduced into the opening from the proximal side of the surface. Where the closure device has a single suture introducing opening, the surface can surround the opening with sufficient coverage over the operator's fingers without fully encircling the closure device. Where the closure device has two or more suture-introducing openings, respective surfaces can surround the openings, or a single surface can surround all openings and extend completely around the body. In an example where the closure device has an even number of suture-introducing openings, the openings may be arranged in pairs, for example on diametrically opposite sides of the body. For such openings, the surface can conveniently extend completely around the body.

In one example of a closure device having a needle-introducing opening, the body of the device may include finger grasping areas for accommodating an operator's fingers. The grasping areas may include surfaces complementary to finger curvature, and may include surface variations for helping the operator to grasp the body of the closure device. The surface variations may be ridges, grooves, knurling, dimples, surface texture variations or other surface variations to help the operator reliably grasp the body of the closure device. In another example of apparatus and methods for closing a tissue opening, for example a trocar opening, a closure device with a passageway for receiving a suture-carrying needle or other closure device includes a surface or other construction adjacent the opening for shielding an operator's fingers from needle sticks. The closure device may also include a slot or other longitudinally extending opening extending from a surface of the body to the passageway. The slot allows the suture to be disengaged from the body of the closure device after the needle or other closure device has carried the suture along the passageway and through a tissue layer. The suture can be disengaged from the passageway while the closure device is still positioned in the trocar opening or during or after the closure device is removed from the trocar opening. In a closure device having a shield for an operator's fingers, the slot may also extend into the shield, thereby permitting separation of the suture from the passageway over the entire length of the passageway. In one example, the slot extends longitudinally of the closure device body, and may also extend partially about a perimeter of the body. Where the closure device includes a plurality of suture-introducing passageways, a respective number of slots, each corresponding to a passageway, permit separation of the suture from the closure device completely from above the shield to below the shield. In a further example of a closure device for closing a tissue opening, for example a trocar opening, the closure device includes a longitudinally extending body having a proximal portion and a distal portion. The distal portion of the closure device body includes one or more projections extending at least partly laterally of the body and having a suture-receiving target material. The target material is resiliently flexible and initially has an un-perforated proximal surface. The target surface is also configured to be capable of being punctured by a needle or other device suitable for carrying a suture multiple times in a given patient in a surgical setting. In one example, the target surface material is selected so as to reliably hold a length of suture using friction between the outer wall of the suture material and target surface material, for example a size 0 suture, under normal operating conditions. A suitable target surface material includes silicone rubber, but may include but be not limited to other commonly available biocompatible thermoset or thermoplastic materials (e.g. Polyurethane, polyethylene, C-flex, and the like) that may consist of a single or compounded materials, suitable to provide the desired friction force to hold and retain the commonly used surgical suture materials. The target material may consist of a single layer material or may be of several layers, each layer having different characteristics or properties designed to achieve the friction necessary to hold the suture in place but at the same time flexible enough to allow any needle or other suture carrying device to penetrate. With the described configuration, specially-configured target materials are not required.

In an additional example of a closure device for closing a tissue opening, for example a trocar opening, the device includes a longitudinally extending body. The body includes a proximal portion and a distal portion, the proximal portion being used for manipulating the closure device and the distal portion for extending within the trocar opening and for making easier the placement and retrieval of one or more sutures. The body further includes one or more indicators or markings for visibly indicating proper location or positioning of the closure device for optimal operation. For example, a visible marking can be used to indicate maximum tissue depth, or maximum depth of the closure device into the tissue. In another example, or in addition, a visible marking can be used as visual warning to the operator that the patient's soft tissue bed may be too insubstantial in terms of thickness and, if the indicator is at or near the skin layer upper surface, that the needle will exit at a point above the skin level instead of below it as desired. In another example, or in addition to one or more of the other markers, a visible marking can be used to indicate desired closure device positioning within a trocar opening relative to a tissue layer to begin or transition the closure device to another configuration. For example, the tissue layer may be the peritoneum, and the visible marking may be used to indicate that a target element for a suture is positioned for deployment. In another example, the visible marking may be used as a visual warning to the operator that the patient's soft tissue bed may be too insubstantial in terms of thickness and, if the indicator is at or near the skin layer upper surface, that the needle will exit at a point above the skin level instead of below it as desired. In a further example, a visible marking may be used to indicate when the closure device has been positioned within the tissue opening, for example relative to a peritoneum layer, to permit the easiest retrieval of a suture that may be held at that time on a part of the closure device.

In a further example of a closure device for closing a tissue opening, for example a trocar opening, the device includes a longitudinally extending body having a proximal portion and a distal portion. The distal portion includes a suture holding portion extending a first distance laterally from a first axial position on the body. The body further includes a substantially straight, suture-receiving passageway extending at an angle to a central axis of a body. The passageway includes an entrance opening and an exit opening on the body distal of the entrance opening and it is substantially aligned with the suture holding portion. The exit opening on the body is positioned proximally at a second axial position relative to the first axial position and spaced therefrom a second distance. The angle of the passageway, the second distance and the first distance are chosen so that a ratio of the second distance to the first distance is no more than preferably approximately 2.5:1. For example, if the suture holding portion is spaced from the body approximately 1 cm, the distance from the first axial position on the body to the exit opening is no more than approximately 2.5 cm. The ratio can be less than 2.5:1, but in one example, the first distance between the first axial position on the body and the suture holding portion is at least 1 cm.

Additionally, if the first distance between the first axial position on the body and the suture holding portion is at least 1 cm, the ratio can be less than 2.5:1, for example by adjusting the second distance or by adjusting the angle of the passageway, or both. Examples of accessories and their use with closure devices for tissue openings, needles or suture introducers can include one or more features for making heir use easier with closure devices. One feature may include a combination of needle length and handle configured such that when the needle is fully introduced into the closure device, the handle or other structure on the needle contacts a structure on the closure device substantially preventing further introduction of the needle into the closure device, and therefore substantially preventing further ingress of the needle into a tissue layer. Such a configuration reduces the possibility of unintended needle stick of a tissue layer, organ or other nearby surface. Additionally, such a configuration in combination with an appropriately-designed closure device for known patient anatomies allows an operator to more confidently follow the closure steps in less time and with fewer redundant steps. Alternatively, a visual marking or position indicia provided in the needle structure may also be used as a means to indicate the depth of the needle during suture introduction.

In another feature for an accessory and its use, such as that for a needle or suture introducer, the needle may include a distal point and a suture-retention structure proximal of the needle point. The retention structure may include a groove or undercut having an entrance opening where the entrance opening is sized larger than the suture and allows loading of the suture into the groove or undercut. The groove or undercut is sized such that the narrowest opening includes a maximum spacing slightly less than the suture diameter to be used with the needle. The maximum spacing is selected so as to reliably hold the suture within the groove when the suture is in a relaxed configuration, and for example under the weight of gravity. However, for a greater force such as might be applied manually, the suture can be removed from the groove and out the opening. Such a greater force would be greater than the force of gravity on the suture hanging from the groove. In the present applications for a needle in use with a closure device, the groove opens distally and has a groove bottom proximal of the opening.

A further feature for an accessory and its use, such as that for a needle or suture introducer having a groove for releasably retaining a suture, the groove is formed in a side of the needle proximal of a distal needle tip. The needle includes an indicator on a side surface of the needle at a proximal portion of the needle, and the indicator is positioned perimetrically with respect to the needle at about the same position as the groove is located. The indicator can be a raised, longitudinally-extending the ridge or land, an arrow, grooves, unique finger holdings or other configurations indicating the groove position. The operator can use the indicator to establish in which radial direction the groove entrance opening is facing when the needle tip is not easily visualized, such as when it has passed through or beyond a tissue layer. This feature is also beneficial to the operator or surgical team when manually loading the suture into the needle groove in an operating room or suite where the lighting has been dimmed or is absent.

Accessories for use with closure devices for tissue openings can incorporate any one or more of the features described herein with respect to a needle or suture introducer. The needle may also include a handle having finger grip surfaces or other manual assist configurations for helping the operator manipulate the needle.

The apparatus described herein, as well as other apparatus, can be used in accordance with one or more methods for closing tissue openings. In the context of using one or more methods with a closure device described herein, such as may be used for closure of abdominal trocar openings, the closure device can be inserted into a trocar opening after the trocar has been removed. In one example, the closure device can be inserted until the skin surface comes adjacent a proximal indicator, for example a circumferential line about the closure body. Additionally, where scope-based visualization s available, clearance of a distal indicator interior to the peritoneum indicates that the target wings or other target elements can be deployed laterally of the closure body. Alternatively, where scope-based visualization is not used or available, the skin surface adjacent the proximal indicator will indicate that the target wings or other target elements can be deployed laterally for most patients. Sutures can then be introduced and closure effected as desired. The apparatus described herein, as well as other apparatus, can be used in accordance with another example of a method for closing tissue openings. Regardless of whether or not the foregoing method of positioning a closure device is used, sutures can be introduced into tissue layers through a closure device using a suture-carrying introducer, for example a needle. The needle can be loaded with a suture manually or automatically by moving a suture portion along the shaft of a needle toward a groove opening at a distal portion of the needle. The suture portion is moved along the shaft proximal to distal or distal to proximal until the suture portion enters the groove opening, for example radially inward from the shaft outer surface, after which the suture portion is moved proximally of the needle tip. The operator may appreciate a tactile sensation when the suture enters the groove opening and also observe it visually depending upon the lighting in the operating room. A slight force is applied to the suture portion to overcome a restriction in the groove opening having a dimension slightly less than an outer dimension of the suture, after which the suture passes the restriction and reaches the bottom of the groove, for example at the proximal-most portion of the groove. The retention of the suture portion in the groove can be tested if desired by directing the needle point downward with the suture also extending downward by gravity. The spacing of the restriction in the groove opening is such that the suture remains within the groove as the force necessary to move the suture portion past the groove restriction is greater than the force of gravity on the suture. The suture can then be introduced, as well as other sutures, into the tissue and closure effected as desired. In additional examples, apparatus such as that described herein as well as other apparatus can be used in accordance with a further example of a method for closing tissue openings. Whether or not any other methods herein of positioning a closure device or loading a suture-carrying introducer are used, a closure device inserted into a trocar opening can be loaded with one or more sutures without requiring the operator to intervene to manually or with additional tools detach a suture from an introducer and attach the suture to the closure device. In one example, the closure device is inserted into the trocar opening with a relatively high friction target material on a distal portion of the closure device, for example below the peritoneum. The target material is high friction relative to the suture material to be used with the closure device. Additionally in one example, the target material is un-perforated prior to initial use and presents a uniform, un-breached surface facing proximally for receiving the suture. The target material is also resiliently flexible, and when a suture introducer, for example a suture-carrying needle, breaches the proximal-facing surface and embeds the suture in the target material, the friction generated in the target material grasps and holds the suture even as the introducer is withdrawn. One exemplary introducer may have a reduced-opening groove for loosely holding a suture portion that can be removed by withdrawing the introducer from the target material. Other sutures may be introduced and closure effected as desired.

In another example of a method for closing a tissue opening, a closure device may be preloaded with one or more sutures and introduced into a tissue opening, for example a trocar opening. When the closure device is suitably inserted, one or more respective wings or suture-holding elements may be deployed substantially laterally of a closure device body. In one example, a suture is releasably positioned and held at least 1 cm laterally away from the closure device body. In another example, a suture may be held in a resiliently flexible material, for example embedded in silicone rubber or other suitable bio-compatible material that provides the desired friction properties in conjunction with the suture. The tissue layer overlying the suture is then pierced with a retriever element, the suture retrieved and then pulled through the tissue layers to a position outside the patient. Similar steps can be followed for retrieving any additional sutures, and then closure completed as desired. Other closure device configurations are also possible for use in this procedure, for example one in which one or more sutures are held by physical restrictions or interference fits between the suture and the suture holder (for example on a wing or other suture-holding element). Additionally, the closure device can include a guide channel or other retriever guide defining the path for the retriever necessary to substantially guarantee contact between the distal tip of the retriever and the target suture, for example even without visualization. Such a guide may be a channel, such as one extending along a line intersecting the target suture position, or a trans-lateral channel extending from one side of the closure device body to the other side and then intersecting the target suture position. A plurality of such guides may be included, for example for respective suture positions.

In a further example of a method for closing a tissue opening, a closure device, including any of those described herein, may be introduced into a tissue opening, for example after removal of a trocar. If the closure device has been properly introduced into the opening, for example as indicated by a proximal indicator being adjacent a skin surface or as indicated by visualization of a distal indicator being inferior to the tissue layer to be closed (for example a peritoneum and abdominal fascia), one or more wings or other suture target elements can be deployed laterally of the closure device body. The target or target elements may be deployed preferably at least 1 cm from the closure device body (measured perpendicular to the body). They are deployed by manipulating an actuator rod relative to the closure device body, such as through manipulator rings or other grasping elements. In one example, the target elements may be locked in an insertion position (un-deployed) until unlocked. Once deployed, the target elements can also be locked in the deployed configuration, for example through re-engagement of a locking element. When the closure device is positioned and configured as desired, the operator can grasp the body of the closure device at a body position distal of suture openings. While grasping the body, a suture carrying introducer is inserted into an opening and guided through tissue to be closed and into a respective target element. In one example, the guide is a trans-lateral passageway with an entrance opening above the operator's grasp on the closure device body and an exit along a line substantially intersecting the suture target. A closure device may be used that has a guard or shield between the operator's grasp on the closure device body and the suture openings.

In the method described in the foregoing paragraph, the suture may be introduced using an introducer with a stop or other element on the introducer that engages a corresponding surface on the closure device that prevents further ingress of the introducer through the tissue and through the target. The introducer may include grasping surfaces and/or alignment indicators for assisting the operator in properly positioning the suture in the target element. The introducer can be removed leaving the suture in the target element, for example embedded in a relatively high friction, resiliently flexible material, for example silicone rubber, and other sutures introduced in a similar manner, if desired. When the desired number of sutures have been embedded in their respective targets, a lock or latch is released and the suture targets returned to their insertion configuration using the manipulator rings or other grasping elements. The closure device can then be withdrawn from the tissue opening carrying with it the suture or sutures previously passed through the desired tissue layer. The tissue layers may then be closed by securing the sutures, and the overlying skin layer may also be closed. In all methods and devices described herein, it is understood that the devices and steps taken to achieve the desired result can be repeated for subsequent closures on the same patient as required.

These and other examples are set forth more fully below in conjunction with drawings, a brief description of which follows.

BRIEF DESCRIPTION OF THE DRAWINGS

FIG. 1 is an upper left front isometric view of a tissue closure device according to one example and a suture introducer according to one example inserted into a guide of the closure device.

FIG. 2 is a left side elevation view of the assembly shown in FIG. 1 including a partial schematic of a tissue layer into an opening in which the closure device may be inserted.

FIG. 3 is a right side elevation view of the assembly of FIG. 1.

FIG. 4 is a lower right rear isometric view of the assembly of FIG. 1.

FIG. 5 is a bottom plan view of the assembly of FIG. 1.

FIG. 6 is a front elevation view of the closure device of FIG. 1.

FIG. 7 is a left side elevation view of the closure device of FIG. 1.

FIG. 8 is a bottom plan view of the closure device of FIG. 1.

FIG. 9 is a top plan view of the closure device of FIG. 1.

FIG. 10 is a longitudinal cross-section view of the closure device taken along 10-10 of FIG. 9.

FIG. 11 is a longitudinal cross-sectional view of the closure device taken along line 11-11 of FIG. 9.

FIG. 12 is a left side elevation of the closure device of FIG. 1 in an insertion configuration.

FIG. 15 is a front elevation view of the body of the closure device of FIG. 1,

FIG. 16 is a side elevation view of the body of the closure device of FIG. 1.

FIG. 17 is a top plan view of the body of the closure device of FIG. 1.

FIG. 18 is a bottom plan view of the closure device of FIG. 1.

FIG. 24 is an upper isometric view of a suture target wing for the closure device of FIG. 1.

FIG. 25 is a bottom plan view of the suture target wing of FIG. 24.

FIG. 26 is a side elevation view of the suture target wing of FIG. 24.

FIG. 27 is a rear elevation view of a suture target wing of FIG. 24.

FIG. 27A is a longitudinal cross section of the target wing of FIG. 27 taken along line 27A-27A.

FIG. 28 is a lower front isometric view of the suture target wing of FIG. 24.

FIG. 29 is a front isometric view of a needle assembly from the assembly of FIG. 1.

FIG. 30 is a front plan view of the needle assembly of FIG. 29.

FIG. 31 is a detailed view of the tip of the needle assembly of FIG. 29 taken at 31-31.

DETAILED DESCRIPTION

Figure 13:
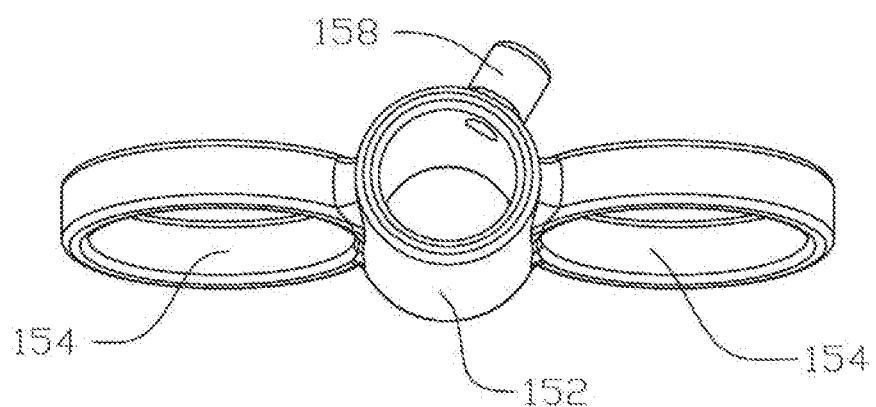
FIG. 13 is an upper isometric view of a slide unit having finger rings for changing the configuration of the closure device of FIG. 1.
Figure 14:
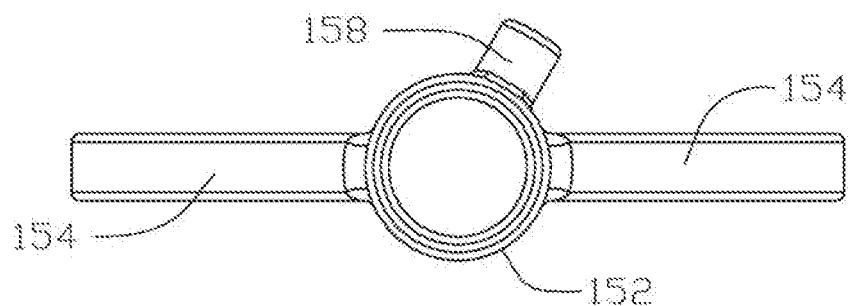
FIG. 14 is a top plan view of the slide unit of FIG. 13.
Figure 19:
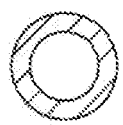
FIGS. 19-23 are transverse cross-sectional views of the closure device body taken along the respective lines in FIG. 16.

This specification taken in conjunction with the drawings sets forth examples of apparatus and methods incorporating one or more aspects of the present inventions in such a manner that any person skilled in the art can make and use the inventions. The examples provide the best modes contemplated for carrying out the inventions, although it should be understood that various modifications can be accomplished within the parameters of the present inventions.

Examples of closure devices and of methods of making and using the closure devices are described. Depending on what feature or features are incorporated in a given structure or a given method, benefits can be achieved in the structure or the method. For example, closure devices using a finger shield or guard may be easier and safer to use. Closure devices having finger grasping surfaces with selected configurations may also help in holding and using the closure device. Closure devices having visual indicator marks also make such closure devices easier and more reliable to use. Moreover, closure devices having predetermined suture delivery configurations may also provide more reliable and consistent bites of appropriate tissue layers desirable for suturing these layers than conventional techniques.

Improvements are also provided to components with which the closure devices may be used. For example, needles or other suture introducers may make it easier to use the closure device where the needle has improved suture holding and release characteristics. They may also be easier to use with needle insertion indicators or stops for reducing the possibility of excessive needle insertion. Indicators on the needles may also be used with suture holding grooves in the needle tip to indicate the relative orientation of the suture holding groove when such grooves are not directly visible to the operator.

These and other benefits will become more apparent with consideration of the description of the examples herein. However, it should be understood that not all of the benefits or features discussed with respect to a particular example must be incorporated into a closure device, component or method in order to achieve one or more benefits contemplated by these examples. Additionally, it should be understood that features of the examples can be incorporated into a closure device, component or method to achieve some measure of a given benefit even though the benefit may not be optimal compared to other possible configurations. For example, one or more benefits may not be optimized for a given configuration in order to achieve cost reductions, efficiencies or for other reasons known to the person settling on a particular product configuration or method.

Examples of a number of closure device configurations and of methods of making and using the closure devices are described herein, and some have particular benefits in being used together. However, even though these apparatus and methods are considered together at this point, there is no requirement that they be combined, used together, or that one component or method be used with any other component or method, or combination. Additionally, it will be understood that a given component or method could be combined with other structures or methods not expressly discussed herein while still achieving desirable results. Closure devices for trocar openings are used as examples of a closure device that can incorporate one or more of the features and derive some of the benefits described herein, and in particular closure devices for abdominal tissue openings. Closure of trocar openings in abdominal walls present particular issues for acceptable results, and closure devices for abdominal openings will be considered in more detail. However, closure devices other than for abdominal wound closures can benefit from one or more of the present inventions.

It should be understood that terminology used for orientation, such as front, rear, side, left and right, upper and lower, and the like, are used herein merely for ease of understanding and reference, and are not used as exclusive terms for the structures being described and illustrated.

In accordance with one example of apparatus that can be used for closing a tissue opening, for example a trocar opening in the abdominal wall, and where the apparatus reflects one or more methods that can be used for tissue closure, a closure device and needle assembly 100 (FIGS. 1-5) includes a closure assembly or closure device 102 and a needle assembly 104. The closure device 102 can be used with the needle assembly 104 as discussed herein, or with other suture introducers or needles, and the needle assembly 104 as discussed herein can be used with other closure devices. However, for purposes of some of the examples, the closure device 102 and the needle assembly 104 will be considered as being used together. Additionally, the present discussion for the application of the closure assembly will be in the context of closure of an abdominal opening, but it should be understood that other tissue closures can be carried out with one or more of the components of the assembly.

In the context of a trocar opening 106 (FIG. 2) in an abdominal wall 108, the opening 106 extends through a skin and superficial layer 110 that may include muscle, depending on the location in the abdomen at which the opening is made. The skin and superficial layer 110 will be referred to as the skin layer 110 for simplicity. Underlying the skin layer 110 is a fascial layer 112 having a thin peritoneum 114 (not separately shown for simplicity). The peritoneum forms the lining of the abdominal cavity outside the internal organs (not shown), and it is through the skin layer 110, fascial layer 112 and peritoneum 114 that the trocar opening and trocar permit access for an operator to the internal organs. Once the surgery is complete, the trocar opening is closed by closing the fascial layer 112 and peritoneal layer 114, while taking care to avoid puncturing or injuring any underlying organs. One way to minimize puncturing underlying organs during the closure process is to retract the tissue layers away from the underlying organs and to limit or carefully control the ingress of suture introducers or retrievers beyond the tissue wall (peritoneal layer), for example in the manner described more fully below.

The closure device 102 in the present example includes a closure body 116 (FIGS. 1-5). The body extends from a proximal portion 118 to a distal portion 120. Generally, the proximal portion 118 is used to control and manipulate the closure device, and the distal portion 120 forms a working structure to be inserted under the peritoneal layer. The distal portion 120 in the present examples is used to present a target at a known and predetermined location where a suture can be reliably placed or retrieved, for example even without visualization, and in such a way that suture bites can be made at optimal locations for forming reliable closures. For example, the distal portion 120 can be used as a target for inserting one or more sutures through the fascial layer 112 and into the target, and in another example, the distal portion 120 can be used as a target for inserting a retrieval tool through the fascial layer 112 to the target for retrieving a pre-disposed suture portion from the target and withdrawing the suture through the fascial layer 112 and a tissue opening 106 to help in closing the opening. The closure device 102 also includes an intermediate or middle portion 122, which will be generally considered that portion of the closure body 116 residing within the opening 106 during normal use. The middle portion 122 generally will extend between the outer surface of the skin layer 110 and the peritoneal layer 114. The middle portion 122 includes at least one element that helps to reliably and repeatably place a suture introducer or retriever at the predetermined target site without the operator having to substantially adjust or vary the direction of movement of the introducer or the retriever. In the present examples, as discussed more fully below, the at least one element in the middle portion 122 that helps to reliably and repeatably place a suture introducer or retriever at the predetermined target site is a channel or passageway, for example a trans lateral passageway, through the body 116 of the closure device.

Considering the closure device 102 in more detail, the distal portion 120 in the present example includes a plurality of suture-receiving elements 124. The elements 124 may be wings that form targets for a suture introducer such as the needle assembly 104. The wings 124 extend outwardly in substantially opposite directions from the closure body 116 in the deployed configuration shown in FIGS. 1-5. They are substantially 180° apart and extend substantially perpendicular to a central axis of the closure body. In other examples, the closure device could have a single wing or plural wings, whether arranged in pairs or otherwise. When arranged in pairs, they can be arranged in two, four, six or more pairs, as desired.

The wings 124 (see also FIGS. 24-28) are pivotally mounted to respective portions of a mounting structure 126 at the distal end of the closure body 116. The wings 124 are mounted at opposite sides of a groove 128 (FIG. 15) centered on the central axis of the closure body, so that the wings can pivot simultaneously between the opened or deployed configuration shown in FIGS. 1-5 and a closed or insertion configuration shown in FIG. 12. The wings 124 are linked to and operated through a pull rod 130 (FIGS. 1-3) through respective link arms or expanders 132. Pull rod 130 extends upward into and is substantially centered on the central axis of the closure body 116 for longitudinal movement within the body. Upward movement of the pull rod 130 pulls the link arms or expanders upward to move the wings 124 from a collapsed or insertion configuration shown in FIG. 12 to the expanded or deployed configuration shown in FIGS. 1-5. Downward movement of the pull rod 130 within the body 116 fold the link arms 132 down relative to the body, thereby pulling the wings 124 downward to the closed configuration.

Suitable precision machining, injection molding, casting or other such forming of the wings, link arms 132 and pull rod 130, and their positioning and mounting to or within the closure body 116 allows accurate positioning of the wings 124 when in the deployed configuration shown in FIGS. 1-5. Therefore, when they are in the deployed configuration, the wing positions are accurately and reliably known relative to other points on the closure device. Likewise, the position of any point on the wings 124 is also accurately and reliably known relative to any other point on the closure device. Therefore, with suitable precision machining or forming of components on the closure device, the precise location of any point on a wing 124 is known and can be used as a target for inserting or receiving a suture. Each wing 124 includes a predetermined target location 134 (FIG. 1).

The target location can be used for reliably receiving a suture portion, for example through an introducer, or for reliably retrieving a suture portion previously placed at the target location. In the present examples, each wing 124 includes a target element 136 securely positioned in the target area 134 of the wing, and partly underneath a target approach opening 138 formed in a top surface 140 of the wing. In the present examples where the introducers or retrievers approach the target opening at an angle, the target approach opening 138 is also formed with a central axis at an angle, substantially parallel or conforming to the angle of approach of the introducer or retriever. The target approach opening 138 includes a wall 142 (FIG. 10) shown as extending substantially parallel to the central axis 142A of the opening. However, the walls can be conical or other selected shape or cross-sectional configuration. The walls are also shown as circular cylindrical, but they can have other configurations as well.

The size and shape of the target approach opening 138 can be determined based on a number of considerations. When used in conjunction with a suture introducer, these considerations may include the suture introducer diameter, the flexibility of the introducer, the travel length of the introducer from an exit port on the closure body 116 to the opening 138, and the desired tolerance between the expected range of motion of the tip of the introducer and the minimum opening cross-sectional configuration.

The target element 136 in the present example is a structure having substantially the same shape as a cavity 143 in the wing 124 and sized sufficiently so that the target element is reliably retained in the cavity.

Alternatively, rather than being pre-cut to size and then assembled, the target element can be insert molded directly into the cavity 143 and can fill the opening 138. The target element 136 is formed from a material sufficiently soft that the suture introducer can traverse and embed the suture in the material. As shown in FIGS. 1-5, the material also is sufficiently soft so that the tip of the introducer can pass through the material. The target element is positioned so as to be substantially centered under the target approach opening 138.

The target element includes a proximally-facing surface 144 (FIG. 10) with which the suture introducer comes into contact. In the present example, the surface 144 is initially unperforated, and lacks any openings, slits, slices or other breaks in the surface to ease the penetration of the introducer past the surface. For situations where multiple closures are required in the same surgical setting and patient, the surface 144 can be used multiple times as long as the target element 136 is able to maintain the embedded suture. The target element for the surface and a substantial portion of the material below the surface is substantially resiliently flexible. In one configuration, the target element is formed from a material that has a sufficiently high coefficient of friction relative to the suture material so as to suitably retain the embedded suture portion during normal operation. For example, it is desirable to ensure that the target element substantially retains the suture all the time while the wings are collapsed and the closure device is being withdrawn from the trocar opening 106. The suture portion can then be cut from the closure device or more simply manually pulled from the target element 136 material to allow an operator to complete the closure of the trocar opening. In one example, the target element is formed from silicone rubber. Other materials (for example biocompatible thermoset and thermoplastic materials) may be used to suitably form the target having the desired characteristics. Additionally, the target material may consist of a single layer material or may be of several layers, each layer having different characteristics or properties designed to achieve the friction desired to hold the suture in place but at the same time flexible enough to allow any needle or other suture carrying device to penetrate.

Figure 20:
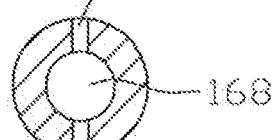
Figure 21:
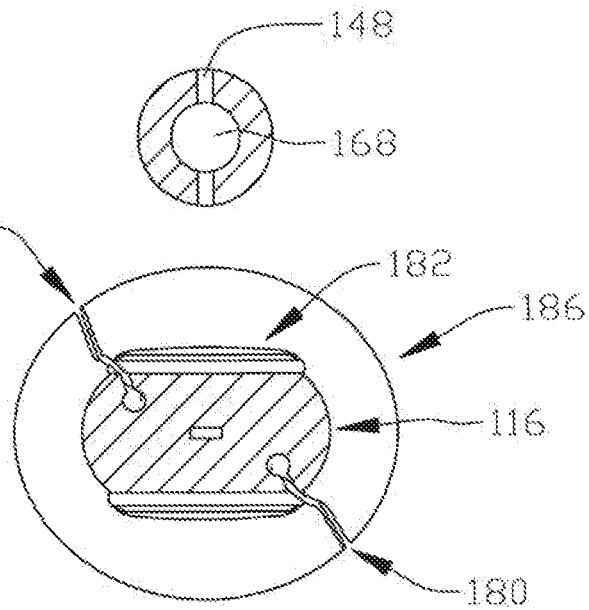
Figure 22:
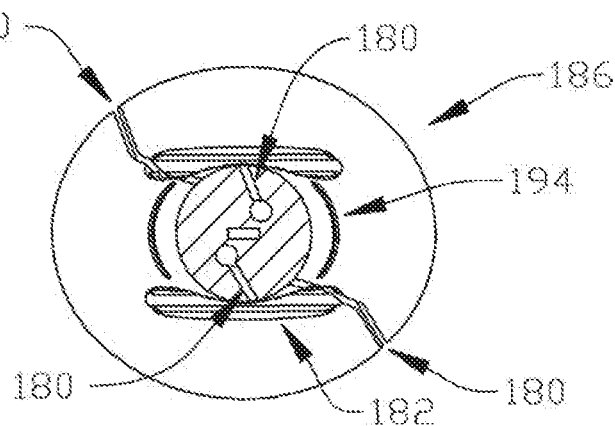
Figure 23:
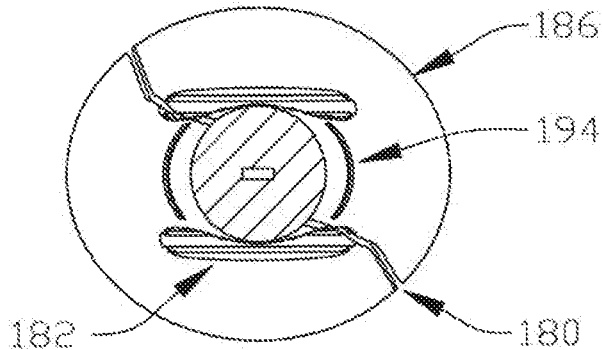

The pull rod 130 (FIGS. 1-11) controlling the positions of the wings can take a number of configurations. In the present example, the pull rod is a substantially straight, longitudinally extending bar having a rectangular cross-section extending from beyond the distal end of the body through a similarly shaped channel in the middle portion and into the proximal portion of the body. The pull rod is positioned on a central axis of the body. The pull rod is substantially rigid so as to reliably transmit a force to enable movement of the wings 124 with minimal to no bending. The proximal end of the pull rod 130 is secured by a pin 146 to an actuator mechanism so that when the actuator mechanism is moved, the pull rod 130 and therefore the wings 124 are also moved. The pin 146 is positioned to move axially within a pair of oppositely formed slots 148 (FIGS. 11 and 16 and 20) in a side wall of the proximal portion of the closure body 116. The slots are formed so as to allow easy translation of the pin within the slots.

In the present example, the pin 146 is fixed to the pull rod and to an actuator sleeve 150 on the closure body 116. The sleeve 150 has a substantially cylindrical body 152 (FIGS. 10-14) configured to slide up and down along an outer surface of the proximal portion of the body. The pull rod 130 and the sleeve 150 are substantially axially fixed relative to each other.

The sleeve 150 is an actuator device that an operator can use to manipulate the wings 124. Manipulator elements such as finger rings 154 on the sleeve 150 make it easier for an operator to move the actuator device up and down over the closure body 116. Other manipulator elements may be used, for example grip surfaces, curved trigger-shaped surfaces and the like. The finger rings 154 are oriented diametrically opposite each other on the sleeve body 152 for convenient manipulation by the operator.

The actuator sleeve 150 may include a biased locking or latching element having a cap or sleeve 156 (FIGS. 1-3, 5, and 12) secured on a boss or post 158 (FIGS. 13-14) on an outside surface of the cylindrical body 152. The locking element 156 in the present example is biased inward and is movable over the post 158 substantially radially relative to the body 116, and includes a locking pin (not shown) fixed to the cap. The locking pin is insertable into and removable from one of two (in the present example) locking openings 160 and 162 (FIGS. 12 and 16). Locking opening 160 locks the sleeve 150 and therefore the wings 124 in a deployed configuration, and the locking opening 162 locks the wings 124 in an insertion configuration such as is shown in FIG. 12. The spring bias in the locking pin keeps the lock in place until manually unlocked, and locks the sleeve 150 in place as soon as the pin is aligned with a given opening 160 or 162. Alternatively, the lock can be a set screw or other manual securement, an umbrella-style latch mechanism, living hinge or the like. The pin 146 in the pull rod and the slots 148 help to keep the sleeve 150 from pivoting about the body so that the locking pin will no longer align with one of the openings 160 or 162.

A top ring 164 (FIGS. 1-7 and 10-12) is fixed to the top of the proximal portion of the body 116. The top ring can be used as a thumb ring by the operator and is oriented so as to extend substantially parallel to the finger rings 154 and substantially orthogonal to the wings 124 when deployed. The operator can use the top ring as a reference or base as to which the actuator sleeve 150 is moved back and forth. A compression spring 166 (FIGS. 10-11) is positioned in a bore 168 and biases the actuator sleeve 150 away from the top ring 164 by way of contact between the spring 166 and the pin 146.

Therefore, the closure device is biased so that the wings are in their insertion configuration (FIG. 12) unless the sleeve 150 is fixed by the locking pin in the opening 160, In the present example, the closure device includes an opening 170 (FIGS. 1, 9 and 17), which opens into a passageway 172. In the present examples, a second passageway 174 includes a respective opening 176 (FIG. 17) substantially identical to but diametrically opposite from the opening 170, Only the opening 170 and the passageway 172 will be described in detail, and it will be understood that the second passageway 174 and second opening 176 are substantially identical to the first. Other openings and passageways may be included to correspond to additional target elements other than the illustrated wings 124 such as are shown in FIG. 1. The opening 170 is formed in the proximal portion of the closure body 116, and the passageway 172 extends from the opening 170 at an angle, for example trans-laterally of the body 116. The passageway terminates at an exit opening 178 (FIGS. 3-4) formed in a side wall of the closure body 116 in the middle portion 122 of the body. Generally, the passageway is substantially straight and includes a center axis that passes through substantially the center of the target access opening 138 in the corresponding wing 124 (FIG. 1). The passageway can be configured in length and cross-sectional dimension in conjunction with a suture introducer such as the needle assembly 104 so that the tip of the needle or suture introducer assembly 104 substantially always passes through the opening 138, even without visualization. Alternatively, the passageway 172 can be slightly curved between the entry opening 170 and exit opening 178.

The opening 170 in the present example opens into a conical or funnel-shaped lead-in or approach to the rest of the passageway 172. The approach makes it easier to introduce the needle assembly 104 to the passageway. The remainder of the passageway to the exit opening 178 has a substantially constant cross-sectional configuration and area until reaching the external surface of the closure body 116. In the present examples, the passageway 172 is substantially circular in cross-section and in one example is sized to smoothly accommodate the needle shaft of the needle assembly 104 and two times the cross-section of a suture to account for a double backed portion of suture, without wear on the suture or binding in the passageway.

As can be seen by comparing FIGS. 1-12, the passageway 172 extends from the opening 170 on one side of the finger rings 154 to the wing 124 on the opposite side of the finger rings. The passageway 172 does not cross the rectangular bore in which the pull rod 130 travels. Additionally, respective passageways do not intersect, thereby ensuring that a subsequent needle passage does not interfere with or damage a previously-positioned suture. The actual length of a passageway may be selected as a function of the vertical height or axial length over which it is desired to have the suture pass through the tissue adjacent the exit opening 178 to the corresponding target area 134. The overall length may also be selected as a function of the axial position of the opening 170. However, as described more fully below, it is desirable to establish a relationship between the axial height from the exit opening 178 to the top of the wing 124 and the lateral distance from the closure body 116 to the center of the target opening 138.

When the closure device 102 is used to pass a suture through the surrounding tissue and into a target area 134, it may include a suture escape slot such as opening 180 extending from the entrance opening 170 to the exit opening 178. The slot opening 180 is a substantially straight opening formed into the wall from the surface of the closure body 116 to intersect the passageway 172 along with the entrance and exit openings 170 and 178, respectively. The slot opening 180 is contained in a plane that also contains the central axis of the passageway 172, Consequently, a suture passing through the passageway 172 can be relatively easily manually extricated from the passageway by the operator by shifting the suture outwardly through the slot opening 180 facilitating a more rapid procedure. The width of the slot opening may be slightly greater than the maximum cross-sectional dimension of the suture. However, the largest gap spacing of the slot opening is less than the smallest cross-sectional dimension of the needle or other introducer element extending along the passageway, so that the suture introducer does not move laterally significantly as it traverses the passageway. Other configurations can omit a suture escape slot. The closure body 116 includes one or more surfaces such as gripping surfaces 182. The gripping surfaces are positioned on a proximal portion of the closure body, and in the present examples below the actuator sleeve 150. The gripping surfaces may be finger grasping or gripping surfaces distal of the openings 170 and 176 but still proximal of the middle portion 122 of the closure body. The gripping surfaces may include surface configurations complementary to finger curvature, and they may include surface variations or textures for helping the operator to reliably grasp the body of the closure device. In the illustrated example, the surface variations include transversely extending ridges 184 (FIGS. 7 and 11). In other configurations, the surface variations may include grooves, knurling, dimples, surface texture variations or other configurations to help the operator reliably grasp the body of the closure device. In the illustrated example, the gripping surface includes curved surfaces as well as surface variations. Additionally, the gripping surfaces include oppositely facing, orthogonal finger grips on the body.

The illustrated example includes, though closure devices can omit one or the other or both, a finger shield or guard 186 around the openings 170 and 176 for the passageways and proximal of the grasping areas. The shield or guard 186 helps to protect the operator's fingers or hand from accidental needle stick as a needle is introduced into one or the other of the openings. In the illustrated example, the guard or shield is partly distal of the openings but still proximal of the middle portion 122 of the body. This allows the operator's finger or fingers to be placed distal of the guard while still above the surface of the skin, and while a suture is being introduced to an opening in the closure device. In the present example, the guard or shield has a flat proximal surface 188 and an elliptical perimeter. The guard or shield is substantially planar and is thick enough to withstand impact and bending during normal use.

In the illustrated example, the openings 170 and 176 are formed in the proximal surface 188 of the guard or shield 186, on substantially diametrically opposite sides of the center axis of the body. The slots 180 also extend through the guard or shield and outward to the perimeter thereof. In the present example, the grasping surfaces 182 are oriented to extend in a direction substantially parallel to the major axis of the elliptical guard or shield, Other configurations and relative dimensions of the gripping surfaces and the guard or shield may also be used.

A substantial portion of the proximal area of the closure body 116 is substantially cylindrical, for example to permit the actuator sleeve 115 to slide along the body surface. Other configurations for the outer surface adjacent the actuator sleeve may also be used while still permitting the actuator sleeve to open and close the wings 124. The finger grasping surfaces are noncircular and non-cylindrical to make easier the grasping and manipulating the closure device. The remainder of the body of the closure device is substantially cylindrical in the perimeter surface, for example to easily accommodate the shape of the trocar opening. The middle portion 122 of the closure body 116 has a substantially straight cylindrical sidewall, except for the slots 180 and the exit openings, and it extends to a first taper surface 190. The taper surface 190 extends distally to a reduced diameter body surface 192 between the taper 190 and the mounting structure 126 for the wings. The taper surface 190 is configured and placed axially on the closure body to permit a portion of the fascial layer 112 ingress against the closure body and further underneath the path of the suture-carrying needle.

The closure body 116 in the present example includes at least one indicator or marker for indicating a location of the closure body relative to surrounding tissue. In the illustrated example, a proximal indicator 194 is formed in at least part of the body surface and extends at least partly around a perimeter of the body at a given axial position on the body. The proximal indicator 194 can be used to provide the operator with an indication of the maximum depth to which the operator should insert the device into the trocar hole relative to the skin layer prior to commencing the closure procedure with the closure device. The proximal indicator in the present example is the most proximal indicator of a plurality of indicators. The proximal indicator helps to reduce the possibility that the closure device or needle or suture introducer component is introduced too great a distance beyond the abdominal wall. The axial position of the proximal indicator away from the closed wings 124 is selected as a function of typical tissue thickness for openings for which the closure devices to be used. Once the maximum tissue depth is reached, visualization or other indicators can be used to confirm if desired that it is appropriate to deploy the wings 124. A proximal indicator can also be used for other purposes.

In the present examples, an intermediate indicator 196 is positioned circumferentially around the closure body 116 in the middle portion 122. The intermediate indicator 196 is positioned slightly below the exit openings, and otherwise substantially encircles the body. The intermediate indicator at the position below the exit openings can be used to note the location of the exit openings for example relative to the fascial layer 112. For example, as can be seen in FIG. 2, the intermediate indicator 196 occurs below the exit openings but above the start of the fascial layer 112. Consequently, introduction of a suture through the fascial layer will have the suture pass through the full thickness of the fascial layer, for example as illustrated in FIG. 2. It is desirable to have the indicator 196 slightly below the exit openings so that the operator can confirm that a suture introduced through the closure device will transit the entire thickness of the fascial layer. This indicator 196 also acts as visual warning to the operator that the patient's soft tissue bed may be too insubstantial in terms of thickness and, if the indicator is at or near the skin layer upper surface, that the needle will exit at a point above the skin level instead of below it as desired, A distal marker or other indicator can be used to indicate a desired position for the closure device within the trocar opening relative to the peritoneal layer to begin or transition the closure device from an insertion configuration to a deployed or open configuration. For example, indicator 198, when visible beyond the peritoneal layer, indicates that the wings 124 have sufficiently cleared the peritoneal layer and can be opened to safely deploy the wings in the typically insufflated abdominal cavity. The wings can then be deployed by pulling up on the finger rings 154, thereby sliding the actuator sleeve 150 proximally to pull up on the pull rod 130.

In a further example, a distal marker 200 (FIG. 16) may be positioned on the body proximal of the body distal end and of the wings 124. The distal marker 200 can be used when the closure device is preloaded with one or more sutures before insertion into the trocar opening. When the wings 124 are preloaded and deployed, and the peritoneal layer is proximal of the distal indicator 200, there is sufficient clearance between the peritoneal layer and the target area 134 on the wings for a retriever such as one with jaws or a clasp to actuate, secure a suture portion, and withdraw the suture portion through the fascial layer and outside the skin layer. Other markers or indicators can also be used as desired. One or more of the indicators may be formed by grooves or other surface discontinuities visible or that can otherwise be sensed on the closure body. The indicators can be painted, pad printed, texturized, or may include some other detectable material or indicator for sensing the position of the indicator relative to the surrounding tissue.

In the example shown in FIG. 2, the proximal indicator 194 and the distal indicator 198 are formed on the closure body 116 to indicate the maximum tissue depth for insertion of the closure device. The spacing between the two indicators is determined by the maximum expected tissue depth for a large population of expected patients, and the two indicators formed accordingly. Other populations such as morbidly obese or exceptionally thin patients may lead to adjustments on the locations of these indicators. The intermediate indicator 198 is positioned axially on the external surface of the closure body slightly below the exit openings for the passageways 172 and 174. The exit openings in turn are positioned on the closure body an axial distance above the deployed level of the wings 124 sufficient to permit traversal by the suture-carrying needle of the entire thickness of the fascial layer 112.

One or more of the indicators can therefore be used for visual or other forms of confirmation for the operator that the positioning of the closure device will achieve the desired suture placement and closure configuration. Similarly, with the closure device having the spacing configuration such that the exit openings are a predetermined distance from the upper level of the deployed wings, and such that the target areas 134 on the wings are spaced a predetermined distance from the adjacent body surface, the operator knows that proper positioning of the closure device will produce the desired suture bite in the fascial layer. Therefore, with the intermediate indicator 196 located slightly below the exit openings, and the distal marker 198 located at the level of the upper wing surfaces, any visual inspection that reveals the peritoneal layer resting on the wings 124 and the intermediate locator 196 above the fascial layer, gives the operator secondary confirmation that the desired suture bite in the fascial layer results.

In one configuration of a closure device 102, such as where the device is used as a target for sutures introduced after the closure device is fully deployed with the wings 124 under the peritoneal layer 114, the closure device 102 can be given a design to achieve a desired suture bite of the fascial layer. For the average patient population, a desired suture bite is one where the suture traverses the peritoneal layer 114 (FIG. 2) about 1 cm from the edge of the trocar opening 106. Therefore, the center of the target access opening 138 in the top of the wing 124 can be positioned a distance 202 of 1 cm measured perpendicular to the adjacent surface of the closure body. Therefore, when the closure device 102 is positioned in the trocar opening as depicted in FIG. 2, the fascial layer 112 closes around the distal portion, including the taper 190 of the closure body. The target access opening 138 is then positioned at the peritoneal layer 1 cm from the adjacent edge of the trocar opening. Likewise, visual inspection will reveal that the distal indicator 198, which is 1 cm away from the target access opening 138, is properly positioned relative to the peritoneal layer, and subsequent insertion of sutures will produce the desired suture bite for the fascial layer.

Likewise in the configuration of the closure device described in the immediately preceding paragraph, for average patient populations, having the exit openings 178 for the suture carriers sufficiently spaced from the tops of the deployed wings 124 will ensure that the sutures will traverse the entire thickness of the fascial layer 112. Therefore, as depicted in FIG. 2, the exit openings 178 of the passageways for the suture carriers are placed a distance 204 axially above the tops of the deployed wings 124 equal to about 2.5 cm. Similarly as depicted in FIG. 2, the suture-carrying needle of the assembly 104 enters the fascial layer 112 well away from the trocar opening wall and traverses the entire thickness of the fascial layer. Likewise, where the fascial layer closes around the tapered portion 190 and the distal portion of the closure body above the wings 124, the suture exits the peritoneal layer about 1 cm outward of the trocar opening wall. Therefore, the distances 202 and 204 can be considered to form a right triangle where the two perpendicular sides have a ratio of 2.5:1. A closure device where the target access opening 138 is 1 cm away from the adjacent body wall and the exit openings are 2 cm above the deployed wings will produce the most desired or optimal suture bite. Therefore, one desired ratio between the perpendicular sides of the triangle is approximately 2.5:1 where the target access opening is on the wing 124 1 cm away from the body. Where the distance 202 is 1 cm, the ratio can be less than 2.5:1 but it is still desirable that the suture traverse the entire thickness of the fascial layer 112. This result is achievable by configuring the closure device with these dimensions and suitable tolerances in the passageways and by configuring the needle assembly 104 so that the needle shaft and its tip as a result do not bend significantly out of the linear path from the exit to the target defined by the passageway 174. The target access opening in other examples can be as little as 0.5 cm and may be as much as 2.0 cm away from the body (measure perpendicularly). Also in other examples, the exit openings can be as close as 1.0 cm above the top of the wings or space as much 4.0 cm away. While the closure device can be designed with other configurations to produce different suture bites, it is believed that the closure devices described can reliably and repeatably produce the desired suture bite and closure configuration. Additionally, while visualization of the indicators or markers is useful for confirming proper positioning, precise manufacture of the closure device and the needle assembly or other introducer assembly can reliably and consistently produce the intended result in the tissue beds likely to be encountered in a clinical setting, A suture introducer can be used with the closer devices discussed herein as well as with other tissue closure devices. One example of a suture introducer includes the needle assembly 104 (FIGS. 29-31). The needle assembly 104 includes a proximal handle portion 300 and a distal needle portion 302. The handle 300 includes a disc-shaped cap 304 having a substantially flat end face and an outer diameter approximately the same as the maximum outer diameter of the rest of the handle. In the present example, the handle 300 includes a pair of oppositely-disposed finger grasping surfaces 306, shaped to optimally conform to curved finger surfaces. The grasping surfaces or textures may include surface variations 308 to help in reliably gripping the handle and manipulating the needle assembly. In this example, the grasping surfaces 306 are positioned immediately distal of the cap 304.

The handle may also include relatively shallow concave surfaces 310 extending on opposite sides of the handle over a substantial length of the handle, and on the same sides as the grasping surfaces 306, The surfaces 310 also help the operator to properly hold and manipulate the needle assembly in a closure procedure.

The needle 302 includes a needle shaft 312 extending over a substantial length of the needle. The needle terminates at a needle tip 314, having a strength and configuration suitable for maintaining the point and strong enough to penetrate the resilient material of the target element 136. The needle 302 extends from the base 316 of the handle over a predetermined length to the tip 314. The base 316 is sized or otherwise configured to contact the shield or guard 186 so that further ingress of the needle is prevented. Therefore, the predetermined length of the needle 302 is selected such that, when the base 316 of the handle contact the guard 186 of the closure assembly, the needle tip 314 extends no more than a predetermined distance beyond the target element 136. In one example, the predetermined distance beyond the target element 136 may be less than or approximately the same as the distance that the pull rod 130 extends below the bottom surfaces of the deployed wings 124. Pre-selecting the amount of exposed needle tip extending beyond the wings 124 helps to reduce the possibility of unintended needle stick, for example of internal organs within the insufflated abdominal cavity. The handle or other parts of the needle assembly can, in addition or instead, have other surfaces for contacting the closure device to limit further ingress of the needle assembly.

The needle includes a distal end portion 318 having a suture retaining or carrying portion in the form of a groove 320. The groove is formed in one side surface of the needle shaft 312 starting at an axial position adjacent where the needle point 314 transitions to the full needle shaft diameter. The groove includes an entrance portion 322 formed in part by a proximally-extending ramp surface 324 and a protrusion 326. The larger spacing between the ramp surface 324 and the protrusion 326 is about several times the diameter of the suture to be used with the needle 302. The smallest spacing between the protrusion 326 and the ramp portion 324 is approximately the diameter of the suture.

The protrusion 326 extends distally from the needle shaft 312 and it is spaced apart from a long side 330 of the groove. The protrusion converges on the open side and on the groove side to a rounded tip 332 to minimize any damage to the suture when the suture contacts the protrusion. The minimum spacing for the groove between the long side 330 and the protrusion side 334 is slightly less than a diameter of the suture to be used with the needle, for example a size 0 suture. The minimum spacing for the groove is selected so that the suture, represented schematically at 336, requires a proximally-directed force to pull the suture past the restriction in the groove, at which point the suture would be depicted in FIG. 31 as squeezed or elongated in the direction of less constriction until the suture is past the restriction. The protrusion 326 can be formed as a rigid section or as a flexible section such that it can be deflected during suture loading or during the release of the suture. For example, the operator or a machine can grasp the suture on opposite sides of the groove and pull the suture into the groove 320 in the proximal direction along the ramp 324 and against the resistive force created by the restrictive spacing between the walls 330 and 334. The restrictive spacing is preferably such as to keep the suture from falling out of the groove by force of gravity if the needle and suture are pointed downward with the suture hanging from the groove 320. The restrictive spacing is selected so that a greater force is required to remove the suture from the groove, and the greater force is on the order of the frictional force developed between a suture portion and the material of the target element 136, such as silicone rubber, when a suture portion is embedded in the target material. The restrictive spacing of the groove can be formed by cutting or otherwise forming the groove to have a dimension smaller than the outer dimension of the suture, biasing the protrusion 332 toward the groove wall 330 or in other ways.

The needle assembly also includes an indicator 338, in the present example on the handle, for indicating the relative orientation of the groove 320 to ease loading of suture especially in dark operating rooms as the groove feature is discrete and could be difficult to see clearly. The indicator can also be used to determine the orientation of the groove and the suture therein when the needle assembly and suture have been introduced into a passageway in the closure device or further into the tissue or target. In the illustrated example, the indicator 338 is a longitudinally extending ridge formed on the handle and extending substantially the full length of the handle. A gap may be formed between sections of the ridge. The indicator 338 may be positioned during use so that the groove 320 and the supported suture in the target element 136 face away from the body 116 of the closure device. One or more of the presently-described apparatus can be used for closing tissue openings using methods described herein, and other apparatus can be used with one or more of these methods as well. In one process, a tissue opening for example one formed by a trocar can be closed by removing the trocar and introducing a closure device into the opening. In a first example, the closure device is not preloaded with any sutures, and in a second example the closure device is preloaded with one or more sutures.

In the first example, a closure device such as that of 102 illustrated in FIGS. 1-12 is placed in the insertion configuration, shown in FIG. 12. The actuator sleeve is placed at a distal position (FIG. 12) and the locking pin of the lock 156 inserted into the distal opening 162 on the closure body (FIG. 16). The wings 124 extend axially of the body and have their respective flat faces facing each other. The closure device 102 is then inserted into the trocar opening 106 until the upper skin layer approaches the proximal indicator 194. If the opening is under visualization, the closure device can be inserted until the distal indicator 198 passes beyond the peritoneal layer 114. Once it is decided that the closure device is inserted sufficiently for deployment of the wings 124, the locking element 156 is withdrawn from the second opening 162 and the actuator sleeve moved proximally until the locking pin can be engaged with the proximal opening 160. As the actuator sleeve translates proximally, the pull rod 130 translates axially in the proximal direction within its rectangular shaft in the body. The pull rod 130 pulls the link arms 132 upward causing wings 124 to pivot about retaining pins through the mounting structure 126 at the distal end of the body. When the locking element 156 engages the proximal opening 160 the wings 124 are fully deployed substantially laterally and perpendicular to the central axis of the body and to the pull rod 130. The upper surfaces 140 of the wings are substantially adjacent the peritoneal layer and the target access openings 138 are aligned with their respective passageways in the body 116.

The needle assembly 104 has been previously loaded with an adequate length of suture 336 by placing a bight of an end portion of the suture on the shaft 312 proximal of the protrusion 332 (FIG. 31). While the suture contacts the side of the needle, the suture is moved distally along the converging surface toward the tip 332 and down into the opening 320. The suture 336 is then moved proximally along the ramp surface 324 and under the protrusion 326 and moved against the groove restriction by application of an increased force until the suture 336 seats in the bottom of the groove. The holding of the suture can be tested by releasing the suture and letting it hang from the groove. The suture-carrying needle can then be introduced into the opening 170 in the closure device as represented in FIGS. 1-5. The operator grasps the closure device at the grasping surfaces 182 and lifts the closure device against the peritoneal layer and separates the tissue layers further away from the underlying organs or other tissues in the abdominal insufflated cavity. With the operator's fingers underneath the shield or guard 186, the needle assembly is inserted into the opening 170 and advanced along the passageway 172 with the needle indicator 338 on the handle oriented as shown in FIGS. 1-5. As the needle tip exits the exit opening 178, the needle tip penetrates the tissue surrounding the trocar opening in the area above the fascial layer 112. As the needle shaft continues along the passageway and the needle tip penetrates further into the tissue, the needle tip approaches the target access opening 138, all the while carrying the loaded suture end portion.

The needle point punctures the proximal facing surface of the target element 136 and continues through the target element until the base 316 of the needle handle bottoms out against the guard 186 or the conical opening 170, as predetermined by the relative sizes and positions of the guard and the handle. If operating under scope-based visualization, suitable embedding of the suture in the target element can be confirmed. The needle assembly can then be withdrawn from the target element, with the frictional engagement between the silicone rubber of the target element and the suture acting to hold the suture embedded in the target element as the needle is withdrawn. The needle assembly is fully withdrawn from the closure device and reloaded with the other end of the suture or another suture (or another needle assembly can be used). While the operator grasps the closure device about the grasping surfaces 182 and lifts the device, the suture-loaded needle assembly 104 is introduced to the second opening 176 and along the second passageway 174 to embed the suture in the target element of the diametrically opposite wing 124 (see phantom needle in FIG. 2). The needle assembly is then withdrawn again. With closure devices having more wings and passageways, the process (procedural steps described above) can be repeated for each one. The locking element 156 is then released and the spring bias moves the actuating sleeve distally, closing the wings 124 until the locking button 156 engages the second opening 162 and locks in place. The closure device holding the embedded suture ends in each wing can then be removed from the trocar opening, also drawing suture into the tissue and out through the trocar opening. The suture lengths residing in the passageways can be removed out of the slots 180 either before or after the closure device is removed from the trocar opening. The embedded sutures can also be manually removed from the silicone rubber target elements in the wings. The sutures can then be tied off as desired to complete the closure.

In the second example process, one or more sutures are first anchored on respective wings of a closure device and then subsequently introduced into a tissue opening, for example a trocar opening. With a pair of wings, a single length of suture can have its ends anchored in respective wings with the connecting loop remaining outside the trocar opening. The suture ends can be anchored on the wings for example by being embedded in a relatively high friction material such as silicone rubber, or by engaging one or more structures on or about the wings such as by interference fit or frictional engagement, by wrapping, by a cleat arrangement, by a miniaturized clamp or by various other active or passive means. In one configuration, a suture end portion is anchored by spaced apart anchor elements on each side of the wing and with the intermediate suture length extending over an open area forming the target area for a grasping or retrieving element. The grasping or retrieving element will then approach the target area, for example with jaws or other grasping mechanisms open to engage the suspended suture portion. The sutures can be left outside the body of the closure device.

The closure device with the sutures mounted and in the insertion configuration is then inserted into the trocar opening until the indicators show that the closure device is sufficiently inserted. The wings are then deployed, and the closure device positioned within the trocar opening to form a gap between the wings and the peritoneal layer. While the operator grasps the closure device at the grasping surfaces 182, a retrieval tool is introduced into the opening 170 and along the passageway 172. The retrieval tool is sufficiently sharp to pierce the tissue layers in order to reach the embedded suture on the associated wing. The retrieval tool may include jaws or other grasping elements for securely holding the suture. Alternatively, the retrieval tool can utilize a groove which enables the operator to let the suture 'run' instead of being grasped when withdrawn as commonly done in orthopedic applications involving sutures. This method would include loading the midsection of the suture, providing an adequate length of suture on the respective anchor elements before insertion of the device. In either embodiment, as the working portion of the retrieval tool exits the peritoneal layer, the working portion is activated, for example by opening jaws, and the tool is advanced to retrieve the midsection of the suture mounted in the anchor element. Once the tool is fully advanced in the passageway, such as up to a stop point, the jaws or other working portion are closed and the suture is either allowed to run or is grasped and withdrawn until it exits the tissue layers and the passageway, and then released once a suture end is visible. The retrieval tool is then inserted into the other passageway to retrieve the other suture element in like manner. These procedural steps can be repeated if multiple wings are used. It is also noted that other mechanical means can be used to retrieve the suture.

When each of the suture end portions have been retrieved and released, the closure device can be reset to the insertion configuration and removed from the trocar opening. Because the sutures are free of the closure device, suture escape slots are neither used nor necessary to remove suture elements from the passageways. Traction draws the free ends of the suture tight with the intermediate loop portion against the opening and the suture ends are then tied off to effect a full thickness closure of the fascial layer.

With a closure device where the suture is anchored on the wings before the closure device is inserted into the trocar opening, the closure device may be configured to have a longer body to provide the gap between the peritoneal layer and the target wings, to thereby accommodate the working portions of the retrieval tool. In this configuration, the distal marker 198 is moved proximally to the distal end of the taper 190, The length of the body, for example the taper, is increased a like amount so that the distal indicator 198 still substantially aligns with the peritoneal layer. Additionally, because the trajectory of the retrieval tool is still determined by the central axis of the passageway 172, which has now shifted axially upward away from the target wings, the target access opening or the target area for the retrieval tool is shifted radially outward from the closure body beyond 1 cm (assuming the angle of inclination of the passageway is unchanged). The actual increase in the distance 202 (FIG. 2) can be calculated as a function of the increase in body length of the closure device.

The closure device can be formed from a number of bio-compatible materials, such as polycarbonate, and the various metal parts may be formed from suitable medical grade materials including stainless steel. The needle handle may also be formed, machined, cast or molded from a suitable biocompatible material. The needle shaft and tip may be formed from a hardened stainless steel or similar material. In some examples, though other dimensions may be used as well, a standard length closure device would have an outside diameter of approximately 12 mm and a 2.5 inch working length, with the passageway exit holes about 0.5 cm above the peritoneum and with the wings producing a lateral bite of about 1 cm. An extra-length device for example may have a 3.5" working length and the exit holes would be about 3 cm from the peritoneum and with the wings provide a lateral bite of about 1 cm. The needle on the needle assembly may have an approximately 10 cm minimum working length with a maximum 2 mm outside diameter.

Having thus described several exemplary implementations, it will be apparent that various alterations and modifications can be made without departing from the concepts discussed herein, Such alterations and modifications, though not expressly described above, are nonetheless intended and implied to be within the spirit and scope of the inventions. Accordingly, the foregoing description is intended to be illustrative only.

The invention claimed is:

1. A tissue closure device comprising:
a longitudinal body having a proximal portion for manual actuation of the device and a distal portion for insertion into an opening in a tissue layer, the distal portion having an outer surface; and
a first suture holding element and a second suture holding element, each supported by the distal portion,
wherein the longitudinal body defines a first passageway between a first proximal opening defined on the proximal portion and a first distal opening defined on the outer surface, and the first passageway is aligned with the first suture holding element when the first suture holding element is in a deployed position,
wherein the first passageway extends at an angle to a central axis of the longitudinal body between the first proximal opening and the first distal opening,
wherein the longitudinal body defines a second passageway between a second proximal opening defined on the proximal portion and a second distal opening defined on the outer surface, and
wherein the second passageway extends at an angle to the central axis of the longitudinal body between the second proximal opening and the second distal opening, and the second passageway is aligned with the second suture holding element when the second suture holding element is in a deployed position.

2. The tissue closure device of claim 1, further comprising a proximal facing surface defining a guard or shield.

3. The tissue closure device of claim 2, wherein the proximal facing surface of the guard or shield is substantially planar.

4. The tissue closure device of claim 2, wherein the proximal facing surface extends laterally of the outer surface.

5. The tissue closure device of claim 2, wherein the proximal facing surface is flat.

6. The tissue closure device of claim 2, wherein the proximal facing surface has an elliptical perimeter.

7. The tissue closure device of claim 2, wherein the proximal portion has a taper distal of the proximal facing surface.

8. The tissue closure device of claim 2, wherein the proximal portion has a grasping surface positioned distal of the proximal facing surface.

9. The tissue closure device of claim 8, wherein the proximal portion has a pair of grasping surfaces on opposing sides of the longitudinal body.

10. The tissue closure device of claim 8, wherein the grasping surface includes grooves, knurling, dimples, and/or surface variations or textures.

11. The tissue closure device of claim 1, further comprising a pull rod extending through the longitudinal body and configured to deploy the first suture holding element and the second suture holding element.

12. The tissue closure device of claim 11, further comprising an actuator connected to the pull rod.

13. The tissue closure device of claim 1, wherein the first proximal opening and the second proximal opening each has a conical or funnel-shaped lead-in.

14. The tissue closure device of claim 1, wherein each of the first suture holding element and second suture holding element is configured to pivot laterally away from the central axis of the longitudinal body to the deployed position.

* * * * *